(12) United States Patent
Rawat et al.

(10) Patent No.: US 9,186,501 B2
(45) Date of Patent: Nov. 17, 2015

(54) SYSTEMS AND METHODS FOR IMPLANTING ELECTRODE LEADS FOR USE WITH IMPLANTABLE NEUROMUSCULAR ELECTRICAL STIMULATOR

(71) Applicant: MAINSTAY MEDICAL LIMITED, Swords, County Dublin (IE)

(72) Inventors: Prashant Brijmohansingh Rawat, Blaine, MN (US); Henry Thomas Demorett, Prior Lake, MN (US); Jason Alan Shiroff, Edina, MN (US)

(73) Assignee: Mainstay Medical Limited, Swords, County Dublin (IE)

( * ) Notice: Subject to any disclaimer, the term of this patent is extended or adjusted under 35 U.S.C. 154(b) by 0 days.

(21) Appl. No.: 14/295,153

(22) Filed: Jun. 3, 2014

(65) Prior Publication Data
US 2014/0288616 A1    Sep. 25, 2014

Related U.S. Application Data

(63) Continuation-in-part of application No. 14/061,614, filed on Oct. 23, 2013, now Pat. No. 9,072,897, and a continuation-in-part of application No. 13/797,100, filed on Mar. 12, 2013.

(60) Provisional application No. 61/659,334, filed on Jun. 13, 2012.

(51) Int. Cl.
*A61N 1/05* (2006.01)
*A61N 1/36* (2006.01)

(52) U.S. Cl.
CPC .......... *A61N 1/36003* (2013.01); *A61N 1/0551* (2013.01); *A61N 1/0558* (2013.01); *A61N1/36067* (2013.01); *A61N 1/36071* (2013.01); *A61N 1/36157* (2013.01); *A61N 1/36167* (2013.01)

(58) Field of Classification Search
CPC ..... A61N 1/05; A61N 1/0551; A61N 1/0558; A61N 1/08; A61N 2001/083
USPC .................................. 607/115–117, 126, 128
See application file for complete search history.

(56) References Cited

U.S. PATENT DOCUMENTS

| | | |
|---|---|---|
| 3,077,884 A | 2/1963 | Bartow, et al. |
| 3,893,463 A | 7/1975 | Williams |

(Continued)

FOREIGN PATENT DOCUMENTS

| | | |
|---|---|---|
| EP | 1 255 583 B1 | 12/2007 |
| WO | WO-2006/133445 A2 | 12/2006 |

(Continued)

OTHER PUBLICATIONS

Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):S192-300. http://www.ncbi.nlm.nih.gov/pubmed/16550448.

(Continued)

*Primary Examiner* — Allen Porter, Jr.
(74) *Attorney, Agent, or Firm* — Foley & Lardner LLP; Christopher C. Bolten; Nicola A. Pisano

(57) ABSTRACT

A system of implanting electrode leads for restoring muscle function to the lumbar spine to treat low back pain is provided. The system provides efficient implantation of the leads, including the ability to verify deployment of anchoring mechanisms on the lead using an impedance assessment, such that the implanted lead may be secured within the patient and used to restore muscle function of local segmental muscles associated with the lumbar spine stabilization system.

14 Claims, 12 Drawing Sheets

(56) References Cited

U.S. PATENT DOCUMENTS

| | | | |
|---|---|---|---|
| 4,026,301 A | 5/1977 | Friedman et al. | |
| 4,342,317 A | 8/1982 | Axelgaard | |
| 4,408,609 A | 10/1983 | Axelgaard | |
| 4,549,556 A | 10/1985 | Tarjan et al. | |
| 4,658,835 A | 4/1987 | Pohndorf | |
| 4,917,093 A | 4/1990 | Dufresne et al. | |
| 5,215,088 A | 6/1993 | Normann et al. | |
| 5,496,345 A | 3/1996 | Kieturakis et al. | |
| 5,501,452 A | 3/1996 | Halvorson | |
| 5,522,854 A | 6/1996 | Ideker et al. | |
| 5,733,307 A | 3/1998 | Dinsdale | |
| 5,741,321 A | 4/1998 | Brennen | |
| 5,916,172 A | 6/1999 | Hodges et al. | |
| 5,957,968 A | 9/1999 | Belden et al. | |
| 6,104,957 A | 8/2000 | Alo et al. | |
| 6,314,325 B1 | 11/2001 | Fitz | |
| 6,319,241 B1 | 11/2001 | King et al. | |
| 6,366,819 B1 | 4/2002 | Stokes | |
| 6,406,421 B1 | 6/2002 | Grandjean et al. | |
| 6,473,654 B1 | 10/2002 | Chinn | |
| 6,516,227 B1 | 2/2003 | Meadows et al. | |
| 6,527,787 B1 | 3/2003 | Fogarty et al. | |
| 6,600,956 B2 | 7/2003 | Maschino et al. | |
| 6,671,557 B1 | 12/2003 | Gliner | |
| 6,735,474 B1 | 5/2004 | Loeb et al. | |
| 6,839,594 B2 | 1/2005 | Cohen et al. | |
| 7,096,070 B1 | 8/2006 | Jenkins et al. | |
| 7,206,641 B2 | 4/2007 | Ignagni et al. | |
| 7,239,918 B2 | 7/2007 | Strother et al. | |
| 7,286,879 B2 | 10/2007 | Wallace | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,337,005 B2 | 2/2008 | Kim et al. | |
| 7,337,006 B2 | 2/2008 | Kim et al. | |
| 7,444,181 B2 | 10/2008 | Shi et al. | |
| 7,447,546 B2 | 11/2008 | Kim et al. | |
| 7,450,993 B2 | 11/2008 | Kim et al. | |
| 7,489,561 B2 | 2/2009 | Armstrong et al. | |
| 7,493,175 B2 | 2/2009 | Cates et al. | |
| 7,502,651 B2 | 3/2009 | Kim et al. | |
| 7,580,753 B2 | 8/2009 | Kim et al. | |
| 7,668,598 B2 | 2/2010 | Herregraven et al. | |
| 7,684,866 B2 | 3/2010 | Fowler et al. | |
| 7,708,763 B2 | 5/2010 | Selover et al. | |
| 7,797,053 B2 | 9/2010 | Atkinson et al. | |
| 7,908,015 B2 | 3/2011 | Lazeroms et al. | |
| 7,917,230 B2 | 3/2011 | Bly | |
| 7,930,039 B2 | 4/2011 | Olson | |
| 8,082,039 B2 | 12/2011 | Kim et al. | |
| 8,170,690 B2 | 5/2012 | Morgan et al. | |
| 8,229,565 B2 | 7/2012 | Kim et al. | |
| 8,229,656 B2 | 7/2012 | Ikushima et al. | |
| 8,249,701 B2 | 8/2012 | Imran et al. | |
| 8,380,318 B2 | 2/2013 | Kishawi et al. | |
| 8,606,358 B2 | 12/2013 | Sachs | |
| 2001/0053885 A1 | 12/2001 | Gielen et al. | |
| 2002/0156513 A1 | 10/2002 | Borkan | |
| 2003/0120328 A1* | 6/2003 | Jenkins et al. | 607/116 |
| 2003/0199938 A1* | 10/2003 | Smits et al. | 607/27 |
| 2004/0111118 A1 | 6/2004 | Hill et al. | |
| 2004/0122482 A1 | 6/2004 | Tung et al. | |
| 2004/0236383 A1 | 11/2004 | Yelizarov | |
| 2005/0080472 A1 | 4/2005 | Atkinson et al. | |
| 2005/0154389 A1 | 7/2005 | Selover et al. | |
| 2006/0009827 A1 | 1/2006 | Kurth et al. | |
| 2006/0106416 A1 | 5/2006 | Raymond et al. | |
| 2006/0111746 A1 | 5/2006 | Foreman et al. | |
| 2006/0111754 A1 | 5/2006 | Rezai et al. | |
| 2006/0184222 A1 | 8/2006 | Camps et al. | |
| 2006/0235484 A1 | 10/2006 | Jaax et al. | |
| 2006/0241716 A1 | 10/2006 | Finch et al. | |
| 2007/0027501 A1 | 2/2007 | Jensen et al. | |
| 2007/0073357 A1 | 3/2007 | Rooney et al. | |
| 2007/0100377 A1 | 5/2007 | Armstrong et al. | |
| 2007/0100391 A1 | 5/2007 | Armstrong | |
| 2007/0100408 A1 | 5/2007 | Gerber | |
| 2007/0100411 A1 | 5/2007 | Bonde | |
| 2007/0135768 A1 | 6/2007 | Carlsen | |
| 2008/0103573 A1 | 5/2008 | Gerber | |
| 2008/0103579 A1 | 5/2008 | Gerber | |
| 2008/0132961 A1 | 6/2008 | Jaax et al. | |
| 2008/0167698 A1 | 7/2008 | Kim et al. | |
| 2008/0183221 A1 | 7/2008 | Burdulis | |
| 2008/0183257 A1 | 7/2008 | Imran et al. | |
| 2008/0228241 A1 | 9/2008 | Sachs | |
| 2009/0112263 A1 | 4/2009 | Pool et al. | |
| 2009/0210041 A1 | 8/2009 | Kim et al. | |
| 2009/0259280 A1 | 10/2009 | Wilkin et al. | |
| 2010/0030227 A1 | 2/2010 | Kast et al. | |
| 2010/0036454 A1 | 2/2010 | Bennett et al. | |
| 2010/0082086 A1 | 4/2010 | Zhu | |
| 2010/0174240 A1 | 7/2010 | Wells et al. | |
| 2011/0224665 A1 | 9/2011 | Crosby et al. | |
| 2011/0224682 A1 | 9/2011 | Westlund et al. | |
| 2011/0251662 A1* | 10/2011 | Griswold et al. | 607/128 |
| 2011/0270340 A1* | 11/2011 | Pellegrini et al. | 607/9 |
| 2012/0035953 A1 | 2/2012 | Armstrong | |
| 2012/0116477 A1 | 5/2012 | Crowe et al. | |
| 2012/0283800 A1 | 11/2012 | Perryman et al. | |
| 2012/0323253 A1* | 12/2012 | Garai et al. | 606/129 |
| 2013/0023974 A1 | 1/2013 | Amrani | |
| 2013/0131766 A1 | 5/2013 | Crosby et al. | |
| 2014/0046398 A1 | 2/2014 | Sachs et al. | |
| 2014/0058476 A1 | 2/2014 | Crosby et al. | |
| 2014/0463998 | 2/2014 | Sachs | |

FOREIGN PATENT DOCUMENTS

| | | |
|---|---|---|
| WO | WO-2006/135791 A2 | 12/2006 |
| WO | WO-2007/051146 A1 | 5/2007 |
| WO | WO-2008/048471 A2 | 4/2008 |
| WO | WO-2009/134475 A1 | 11/2009 |
| WO | WO-2012/057916 A1 | 5/2012 |
| WO | WO-2012/091747 A1 | 7/2012 |

OTHER PUBLICATIONS

Baker et al., "Clinical Uses of Neuromuscular Electrical Stimulation," NeuroMuscular Electrical Stimulation —A Practical Guide, 4th ed. Rancho Los Amigos Research and Education Institute Inc., pp. 47-66 (2000).

Bhadra et al., "Peripheral nerve stimulation for restoration of motor function," Journal of Clinical Neurophysiology: Official Publication of the American Electroencephalographic Society, 14(5):378-33 (Sep. 1997).

Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).

Bowman et al., "Effects of Waveform Parameters on Comfort during Transcutaneous Neuromuscular Electrical Stimulation," Annals of Biomedical Engineering, 13:59-74 (1985).

Bradford et al., "Surface Electrical Stimulation in the Treatment of Idiopathic Scoliosis: Preliminary Results in 30 Patients," Spine, 8(7):757-764 (1983).

Brazier et al., "A Comparison of the EQ-5D and SF-6D Across Seven Patient Groups," Health Economics, 13:873-884 (2004).

Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.

Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.nlm.nih.gov/pubmed/22256103.

(56) References Cited

OTHER PUBLICATIONS

Crago et al., "The choice of pulse duration for chronic electrical stimulation via surface, nerve, and intramuscular electrodes," Annals of Biomedical Engineering, 2(3):252-264 (1974).
Criterion Inc., "NMES Treatment Protocols," 3 pages (accessed Jun. 7, 2012) available at http://www.criterionmed.com/PDF/NMES%20Treatment%20Protocols.pdf.
Durham et al., "Surface Electrical Stimulation Versus Brace in Treatment of Idiopathic Scoliosis," Spine, 15(9):888-891 (1990).
EMPI, "Low Back Syndrome/Chronic Low Back Pain," NMES Guidelines for Treatment, 2 pages (2003).
Extended European Search Report dated Jan. 7, 2013 in related European Patent Application No. 12176863.
Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.
Freeman, et al., The Role of the Lumbar Multifidus in Chronic Low Back Pain: A Review, American Academy of Physical Medicine and Rehabilitation, 2:142-146 (2010).
Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).
Garmirian, et al., Discriminating Neurogenic from Myopathic Disease via Measurement of Muscle Anisotrophy, Muscle Nerve, 39(1):16-24 (2009) (Abstract only).
Glaser et al., "Electrical Muscle Stimulation as an Adjunct to Exercise Therapy in the Treatment of Nonacute Low Back Pain: A Randomized Trial," The Journal of Pain, 2(5):295-300 (2001).
Gorman et al., "The effect of stimulus parameters on the recruitment characteristics of direct nerve stimulation," IEEE Transactions on Bio-medical Engineering, 30(7):407-414 (1983).
Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following intervertebral disc lesion," Progress in Motor Control Vi—Brazil. 36:2-3 (2007).
Hodges, et al., Intervertebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Keller, et al., Muscular Contributions to Dynamic Dorsoventral Lumber Spine Stiffness, Eur. Spine J., 16(2):245-54 (2007).
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Miyatani, et al., Validity of Estimating Limb Muscle Volume By Bioelectrical Impedance, J. Appl. Physiol., 91:386-394 (2001).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/10.1111/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
PCT International Search Report and Written Opinion dated Sep. 3, 2013 in related PCT Application No. PCT/US2013/045223.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/articleviewer.aspx?year=1997&issue=00930&article=00002&type=abstract.
RS Medical, "RS-4M Muscle Stimulator," available at http://www.rsmedical.com/documents/fact_sheet_RS4m.pdf (last visited Jul. 19, 2012).
Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Solomonow et al., "The Ligamento-Muscular Stabilizing System of the Spine," Spine, (1998), 23(23):2552-2562.
Spinal Fusion Guidelines, MD Guidelines, 2009. www.mdguidelines.com/spinal-fusion.
Stokes, et al., "Surface EMG Electrodes Do Not Accurately Record from Lumbar Multifidus Muscles," Clin. Biomech, (2003), 18(1):9-13 (Abstract Only).
Van Dieen, et al., "Trunk Muscle Recruitment Patterns," Spine, (2003), 28(8):834-841 (Abstract Only).
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.
Van Zundert et al., "Radiofrequency treatment for chronic pain syndromes," CPD Anaesthesia, 6(1):13-17 (2004).

(56) References Cited

OTHER PUBLICATIONS

Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.

Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAI&dq=Application of Muscle/Nerve Stimulation in Health and Disease&ots=CMV5rXiDQD&sig=Wg8u1YOC4PgyVDzcjdwBub5U2To (Accessed Jun. 2, 2011).

Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.

Ward et al., "Architectural analysis and intraoperative measurements demonstrate the unique design of the multifidus for lumbar spine stability," J. Bone Joint Surg. [Am.] 91:176-185, PMC2663324 (2009).

Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).

Partial International Search Report dated Aug. 4, 2015 in Int'l PCT Patent Appl Serial No. PCT/US2015/032732.

* cited by examiner

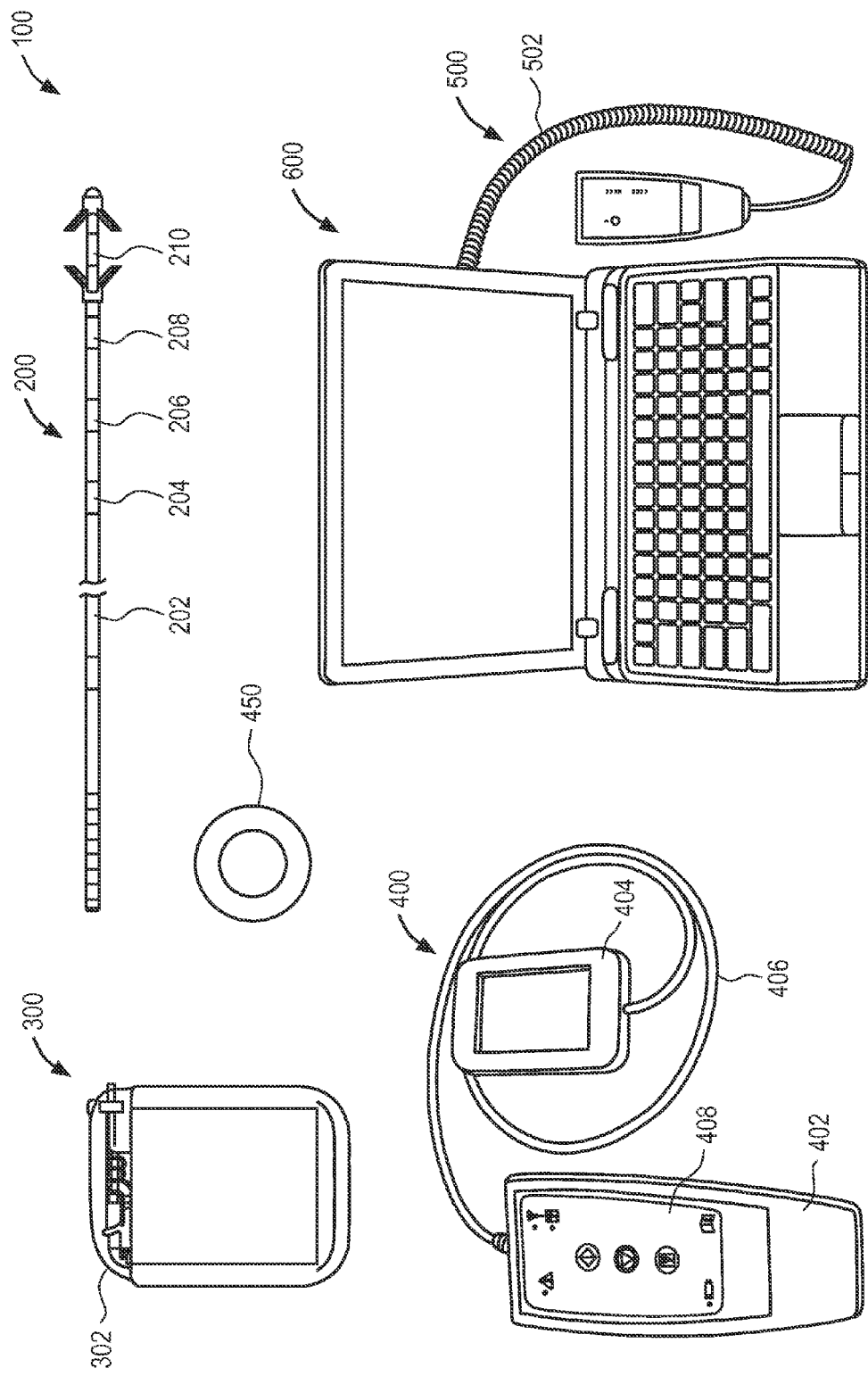

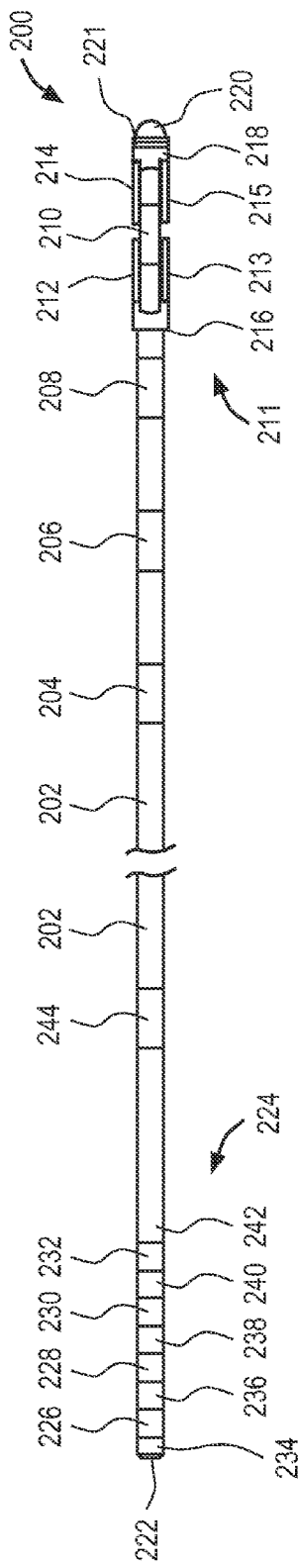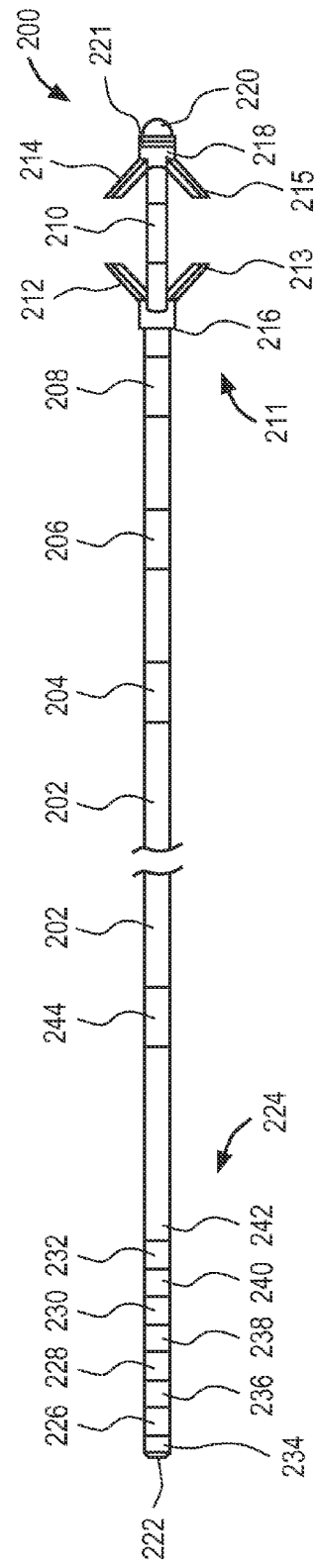

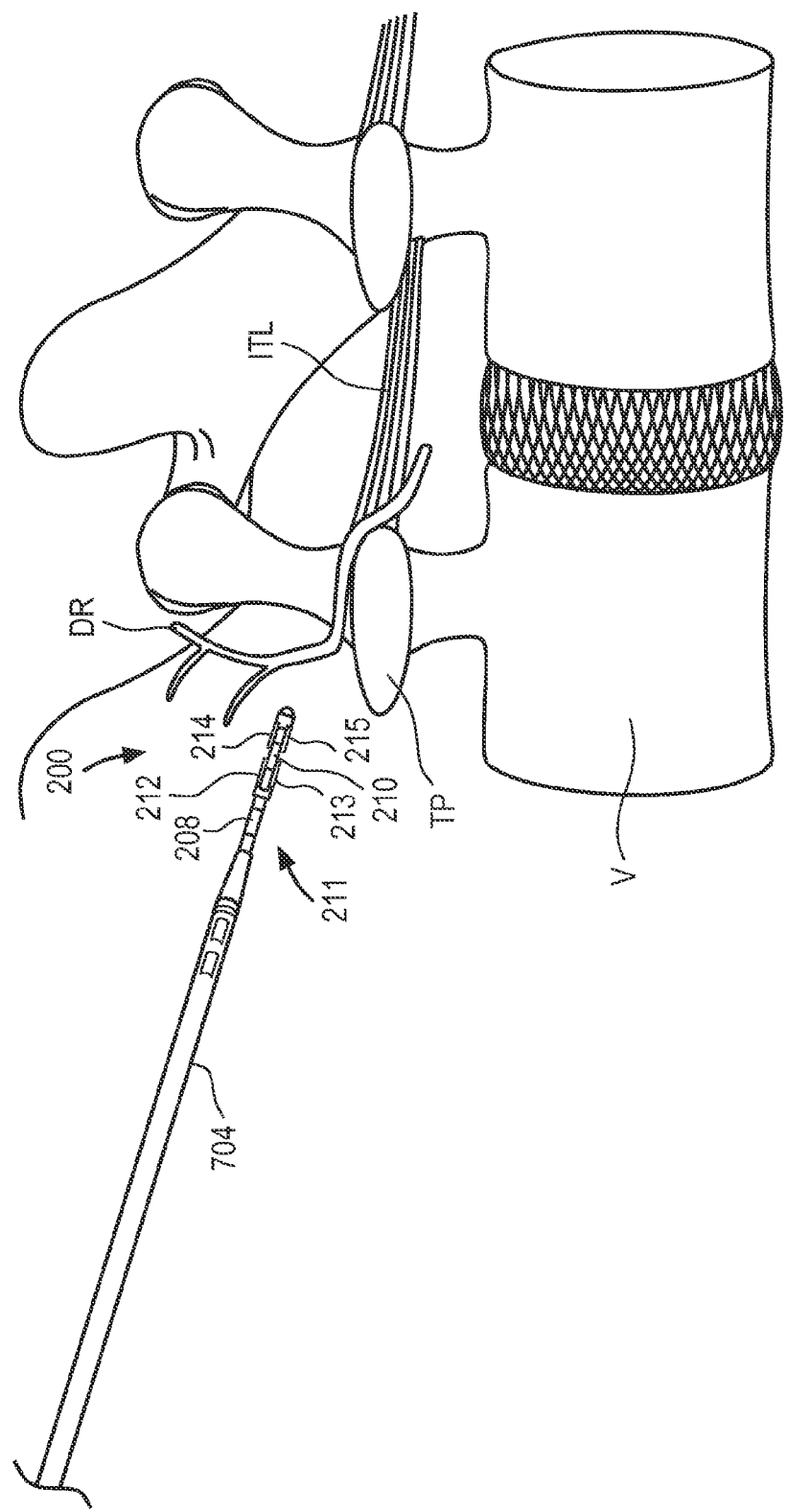

SYSTEMS AND METHODS FOR IMPLANTING ELECTRODE LEADS FOR USE WITH IMPLANTABLE NEUROMUSCULAR ELECTRICAL STIMULATOR

I. CROSS-REFERENCE TO RELATED APPLICATIONS

This application is a continuation-in-part application of U.S. patent application Ser. No. 14/061,614, filed Oct. 23, 2013, the entire contents of which is incorporated herein by reference. This application is also a continuation-in-part application of U.S. patent application Ser. No. 13/797,100, filed Mar. 12, 2013, which claims the benefit of priority of U.S. Provisional Application Ser. No. 61/659,334, filed Jun. 13, 2012, the entire contents of each of which is incorporated herein by reference.

II. FIELD OF THE INVENTION

This application generally relates to systems and methods for implanting electrode leads for neuromuscular electrical stimulation, including stimulation of tissue associated with control of the lumbar spine for treatment of back pain.

III. BACKGROUND OF THE INVENTION

The human back is a complicated structure including bones, muscles, ligaments, tendons, nerves and other structures. The spinal column has interleaved vertebral bodies and intervertebral discs, and permits motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain in the lower or lumbar region of the back is common. In many cases, the cause of back pain is unknown. It is believed that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system may be conceptualized to include three subsystems: 1) the spinal column, which provides intrinsic mechanical stability; 2) the spinal muscles, which surround the spinal column and provide dynamic stability; and 3) the neuromotor control unit, which evaluates and determines requirements for stability via a coordinated muscle response. In patients with a functional stabilization system, these three subsystems work together to provide mechanical stability. It is applicant's realization that low back pain results from dysfunction of these subsystems.

The spinal column consists of vertebrae and ligaments, e.g. spinal ligaments, disc annulus, and facet capsules. There has been an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the ligaments, facet capsules, disc annulus, and other connective tissues. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability must be increased to compensate and maintain stability.

Muscles provide mechanical stability to the spinal column. This is apparent by viewing cross section images of the spine, as the total area of the cross sections of the muscles surrounding the spinal column is larger than the spinal column itself. Additionally, the muscles have much larger lever arms than those of the intervertebral disc and ligaments.

Under normal circumstances, the mechanoreceptors exchange signals with the neuromuscular control unit for interpretation and action. The neuromuscular control unit produces a muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain inactive, or contracting out of sequence with other muscles. As muscles participate in the feedback loop via mechanoreceptors in the form of muscle spindles and golgi tendon organs, muscle dysfunction may further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments is an example of a muscle of the local system. Another example is the transverse abdominus, with its direct attachments to the lumbar vertebrae through the thoracolumbar fascia.

The multifidus is the largest and most medial of the lumbar back muscles. It has a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles that attach to the mamillary processes attach to the capsules of the facet joints next to the mamillary processes. The fasicles arriving from the spinous process of a given vertebra are innervated by the medial branch of the dorsal ramus that issues from below that vertebra.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the oblique internus abdominus, the obliquus externus abdmonimus, the rectus abdominus, the lateral fibers of the quadratus lumborum, and portions of the erector spinae.

Normally, load transmission is painless. Over time, dysfunction of the spinal stabilization system is believed to lead to instability, resulting in overloading of structures when the spine moves beyond its neutral zone. The neutral zone is a range of intervertebral motion, measured from a neutral position, within which the spinal motion is produced with a minimal internal resistance. High loads can lead to inflammation, disc degeneration, facet joint degeneration, and muscle fatigue. Since the endplates and annulus have a rich nerve supply, it is believed that abnormally high loads may be a cause of pain. Load transmission to the facets also may change with degenerative disc disease, leading to facet arthritis and facet pain.

For patients believed to have back pain due to instability, clinicians offer treatments intended to reduce intervertebral motion. Common methods of attempting to improve muscle strength and control include core abdominal exercises, use of a stability ball, and Pilates. Spinal fusion is the standard surgical treatment for chronic back pain. Following fusion, motion is reduced across the vertebral motion segment. Dynamic stabilization implants are intended to reduce abnormal motion and load transmission of a spinal motion segment, without fusion. Categories of dynamic stabilizers include interspinous process devices, interspinous ligament devices, and pedicle screw-based structures. Total disc replacement and artificial nucleus prostheses also aim to improve spine stability and load transmission while preserving motion.

There are a number of problems associated with current implants that aim to restore spine stabilization. First, it is difficult to achieve uniform load sharing during the entire range of motion if the location of the optimum instant axis of rotation is not close to that of the motion segment during the entire range of motion. Second, cyclic loading of dynamic stabilization implants may cause fatigue failure of the implant, or the implant-bone junction, e.g. screw loosening. Third, implantation of these systems requires surgery, which may cause new pain from adhesions, or neuroma formation. Moreover, surgery typically involves cutting or stripping ligaments, capsules, muscles, and nerve loops, which may interfere with the spinal stabilization system.

Functional electrical stimulation (FES) is the application of electrical stimulation to cause muscle contraction to re-animate limbs following damage to the nervous system such as with stroke or spine injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and the control system for each muscle as well as the system as a whole to produce the desired action such as standing and walking.

With normal physiology, sensors in the muscle, ligaments, tendons and other anatomical structures provide information such as the force a muscle is exerting or the position of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle.

Neuromuscular Electrical Stimulation (NMES) is a subset of the general field of electrical stimulation for muscle contraction, as it is generally applied to nerves and muscles which are anatomically intact, but malfunctioning is a different way. NMES may be delivered via an external system or, in some applications, via an implanted system.

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

U.S. Pat. Nos. 8,428,728 and 8,606,358 to Sachs, both assigned to the assignee of the present invention, and both incorporated herein in their entireties by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to reactivate the motor control system and/or strengthen the muscles that stabilize the spinal column, which in turn is expected to reduce persistent or recurrent pain.

While the stimulator systems described in the Sachs patents seek to rehabilitate the multifidus and restore neural drive, use of those systems necessitates the implantation of one or more electrode leads in the vicinity of a predetermined anatomical site, such as the medial branch of the dorsal ramus of the spinal nerve to elicit contraction of the lumbar multifidus muscle. For lead implantation using the Seldinger technique, it has been proposed to insert a needle in the patient's back, insert a guidewire through a lumen in the needle, remove the needle, insert a sheath over the guidewire, remove the guidewire, insert the electrode lead through a lumen of the sheath, and remove the sheath. Such a process requires many instruments and can be quite time consuming.

It would therefore be desirable to provide systems and methods for implanting an electrode lead in a more efficient manner.

IV. SUMMARY OF THE INVENTION

The present invention overcomes the drawbacks of previously-known systems by providing systems and methods for implanting an electrode lead. The lead may be configured to restore muscle function to the lumbar spine to treat, for example, low back pain. The systems and methods are expected to provide efficient implantation of the lead, including the ability to verify deployment of anchoring mechanisms on the lead based on impedance measurements, such that the implanted lead may be secured within the patient and used to restore muscle function of local segmental muscles associated with the lumbar spine stabilization system.

In accordance with one aspect, a system for restoring muscle function to the lumbar spine is provided. The system may include first and second electrodes configured to be implanted in or adjacent to tissue associated with control of the lumbar spine, a lead having the first and second electrodes disposed thereon, a fixation element coupled to the lead and disposed in proximity to the first electrode, a pulse generator coupled to the first and second electrodes via the lead, and software stored on a non-transient computer readable media configured to run on an external computer operatively coupled to the pulse generator. The fixation element may be configured to transition from a delivery state, wherein the fixation element is positioned adjacent to the first electrode, to a deployed state, wherein the fixation element is spaced apart from the first electrode and is positioned to anchor the lead to an anchor site, e.g., muscle. The pulse generator may be configured to cause the first or second electrode to emit energy such that the second or first electrode, respectively, receives a portion of the emitted energy. The pulse generator may be further configured to transmit a signal indicative of an impedance measurement based on the energy emitted (e.g., from the first or second electrode) and the portion of the energy received (e.g., at the second or first electrode). The software may be configured to cause the external computer to display the impedance measurement indicative of whether the fixation element is in the delivery state or the deployed state.

The system may further include a second fixation element coupled to the lead distal to the fixation element, wherein the fixation element is angled distally relative to the lead and the second fixation element is angled proximally relative to the lead. The fixation element and the second fixation element may be configured to sandwich the anchor site therebetween.

The system also may include an external programmer coupled to the external computer, where the external programmer is configured to receive the signal indicative of the impedance measurement from the pulse generator and to transmit the signal to the external computer. In addition, the external programmer may be configured to transfer programming data to the pulse generator. The software may be configured to permit selection, adjustment, and display of the programming data. The programming data may include at least one of: pulse amplitude, pulse width, stimulation rate, stimulation frequency, ramp timing, cycle timing, session timing, or electrode configuration. The software may be configured to determine whether the fixation element is in the delivery state or the deployed state.

The system further may include a handheld activator configured to transfer a stimulation command to the pulse generator, wherein the stimulation command directs at least one of the first or second electrodes to stimulate the tissue in accordance with the programming data.

The software may be configured to cause the external computer to display a second impedance measurement based on a second signal. The impedance measurement and the second impedance measurement may be compared, e.g., by a physician or by the software, to determine whether the fixation element is in the delivery state or the deployed state. In one embodiment, the impedance measurement is indicative of the fixation element being in the delivery state in a range; e.g., between 1501-3500 ohms, 1200-2500 ohms, 1000-2000 ohms, or 750-1750 ohms; and the impedance measurement is indicative of the fixation element being in the deployed state in a different range; e.g., between 500-1500 ohms, 500-1200 ohms, 500-1000 ohms, or 500-750 ohms. Also, the lead may be configured to be delivered through a sheath.

In accordance with another aspect, a method of verifying deployment of a fixation element in a system for restoring muscle function to the lumbar spine is provided. The method may include implanting a lead such that an electrode disposed on the lead is positioned in or adjacent to tissue associated with control of the lumbar spine, the lead coupled to a fixation element disposed in proximity to the electrode, the fixation element configured to transition from a delivery state, wherein the fixation element is positioned adjacent to the electrode, to a deployed state, wherein the fixation element is spaced apart from the electrode and is positioned to anchor the lead to an anchor site; causing the electrode to stimulate tissue using a pulse generator; transmitting a signal indicative of an impedance measurement to an external display; displaying the impedance measurement on the external display; and determining whether the fixation element is in the delivery state or the deployed state based on the displayed impedance measurement.

The signal may be transmitted from the pulse generator to an external programmer coupled to an external computer having the external display. The method may further include adjusting the lead if the fixation element is determined to be in the delivery state.

In accordance with yet another aspect, a kit for implanting an electrode lead in a system for restoring muscle function to the lumbar spine is provided. The kit may include a sheath configured for insertion in a lower back of a patient, a needle electrode, and a lead having an electrode at a distal end of the lead. The sheath has a lumen extending therethrough. The needle electrode has a distal end configured to be positioned in or adjacent to tissue associated with control of the lumbar spine through the lumen. The needle electrode may be configured to stimulate the tissue to permit verification of needle electrode positioning. The lead may be configured for implantation through the lumen to position the electrode in or adjacent to the tissue associated with control of the lumbar spine.

The sheath may include a window and the needle electrode may be configured to stimulate the tissue through the window. The kit may further include an implantable pulse generator configured to be coupled to the electrode via the lead.

In accordance with another aspect, a method of implanting an electrode lead is provided. The method may include inserting a needle electrode disposed within a lumen of a sheath into a patient such that a distal end of the needle electrode is positioned in or adjacent to tissue associated with control of the lumbar spine; stimulating the tissue with the needle electrode; verifying placement of the distal end of the needle electrode at the tissue; removing the needle electrode from the sheath; inserting an electrode lead through the lumen of the sheath such that an electrode disposed on the lead is implanted in or adjacent to the tissue associated with control of the lumbar spine; and removing the sheath. Advantageously, a guidewire need not be used for inserting the needle electrode or inserting the electrode lead. The method may further include stimulating the tissue with the electrode to rehabilitate function of a multifidus muscle and improve spinal stability.

V. BRIEF DESCRIPTION OF THE DRAWINGS

FIG. 1 is a schematic view of an exemplary embodiment of a stimulator system constructed in accordance with the principles of the present invention.

FIGS. 2A and 2B show an exemplary electrode lead of the stimulator system of FIG. 1, wherein fixation elements of the lead are shown in a delivery state in FIG. 2A and in a deployed state in FIG. 2B.

FIGS. 6A through 6F show an exemplary method for implanting the electrode lead of the stimulator system of FIG. 1 using the kit of FIG. 4.

VI. DETAILED DESCRIPTION OF THE INVENTION

Figure 3:
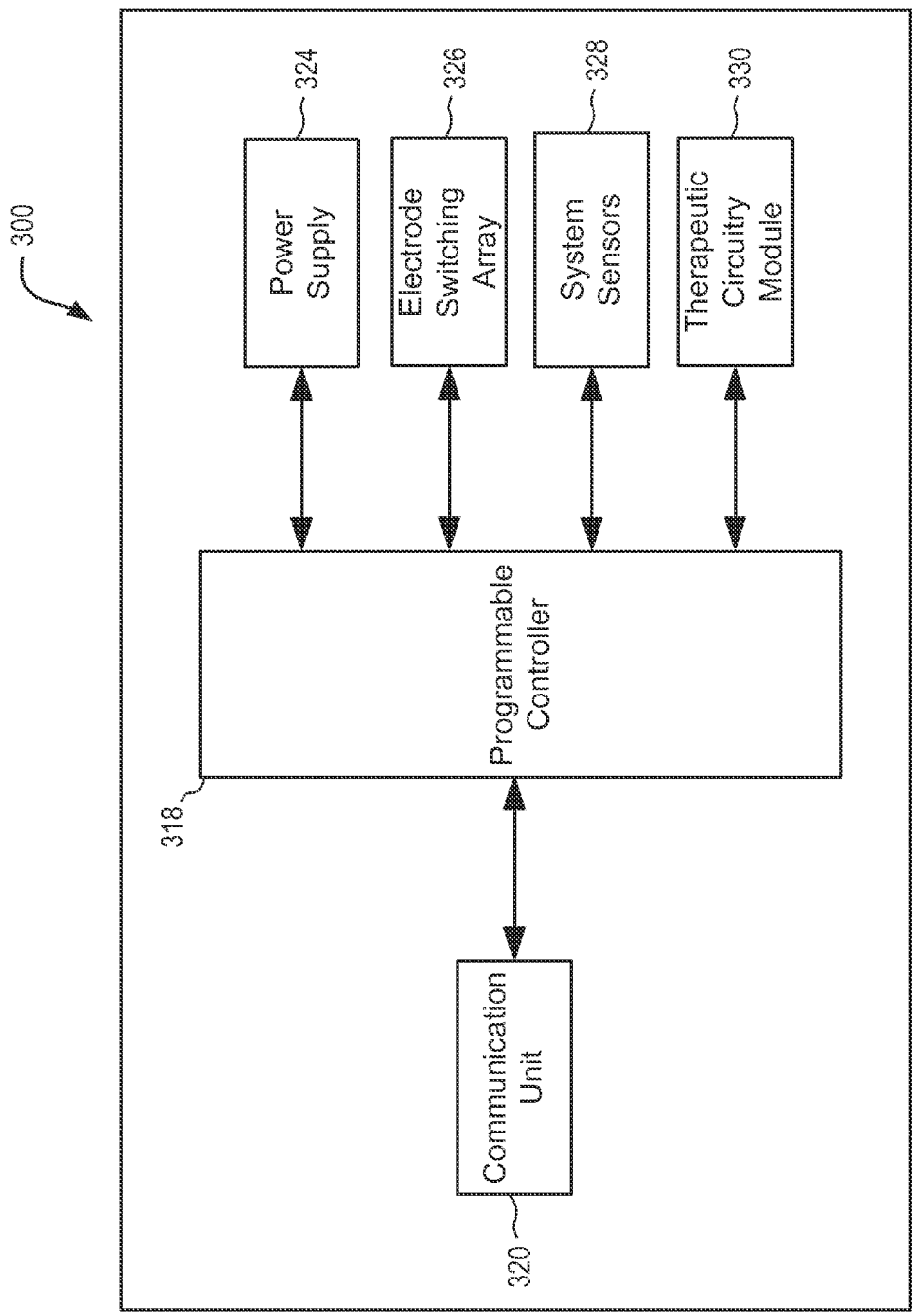
FIG. 3 shows a generalized block diagram of an exemplary implantable pulse generator (IPG) of the stimulator system of FIG. 1.

The neuromuscular stimulation system of the present invention comprises implantable devices for facilitating electrical stimulation to tissue within a patient's back and external devices for wirelessly communicating programming data and stimulation commands to the implantable devices. The devices disclosed herein may be utilized to stimulate tissue associated with local segmental control of the lumbar spine in accordance with the programming data to rehabilitate the tissue over time. In accordance with the principles of the present invention, the stimulator system may be optimized for use in treating back pain in the region of the lumbar spine.

Provided herein are systems and methods for implanting an electrode lead(s) of the neuromuscular stimulation system. The systems and methods are expected to provide efficient implantation of the lead, including the ability to verify deployment of anchoring mechanisms on the lead, such that the implanted lead may be secured within the patient.

Referring to FIG. 1, an overview of an exemplary stimulator system constructed in accordance with the principles of the present invention is provided. In FIG. 1, components of the system are not depicted to scale on either a relative or absolute basis. Stimulator system 100 may include electrode lead 200, implantable pulse generator (IPG) 300, activator 400, optional magnet 450, external programmer 500, and software-based programming system 600.

Electrode lead 200 includes lead body 202 having a plurality of electrodes, illustratively, electrodes 204, 206, 208, and 210. Electrode lead 200 is configured for implantation in or adjacent to tissue, e.g., nervous tissue, muscle, a ligament, and/or a joint capsule, including tissue associated with local segmental control of the lumbar spine. Electrode lead 200 is coupled to IPG 300, for example, via connector block 302. IPG 300 is configured to generate pulses such that electrodes 204, 206, 208, and/or 210 deliver neuromuscular electrical stimulation ("NMES") to target tissue. In one embodiment, the electrodes are positioned to stimulate a peripheral nerve where the nerve enters skeletal muscle, which may be one or more of the multifidus, transverse abdominus, quadratus lumborum, psoas major, internus abdominus, obliquus externus abdominus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

IPG 300 may be controlled by, and optionally powered by, activator 400, which includes control module 402 coupled to pad 404, e.g., via cable 406. Control module 402 has user interface 408 that permits a user, e.g., patient, physician, caregiver, to adjust a limited number of operational parameters of IPG 300 including starting and stopping a treatment session. Control module 402 communicates with IPG 300 via pad 404, which may comprise an inductive coil or RF transceiver configured to communicate information in a bidirectional manner across a patient's skin to IPG 300 and, optionally, to transmit power to IPG 300. For example, a controller within control module 402 may send a stimulation command(s) responsive to user input received at user interface 408 to a controller of IPG 300 via respective telemetry (or RF) systems in activator 400 and IPG 300. The stimulation commands may include, for example, at least one of: a command to start a treatment session or stop the treatment session; a command to provide a status of IPG 300; or a request to conduct an impedance assessment. In a preferred embodiment, a limited number of stimulation parameters may be adjusted at user interface 408 to minimize the chance of injury caused by adjustments made by non-physician users. In an alternative embodiment, the controller of activator 400 also may send adjustments to stimulation parameters, e.g., pulse amplitude (voltage or current), pulse width, stimulation rate, stimulation frequency, ramp timing, cycle timing, session timing, and electrode configuration to IPG 300 responsive to user input received at user interface 408.

Stimulator system 100 also may include optional magnet 450 configured to transmit a magnetic field across a patient's skin to IPG 300 such that a magnetic sensor of IPG 300 senses the magnetic field and IPG 300 starts or stops a treatment session responsive to the sensed magnetic field.

In FIG. 1, software-based programming system 600 is installed and runs on a computer, e.g., conventional laptop, and is used by the patient's physician together with external programmer 500 to provide programming to IPG 300. During patient visits, external programmer 500 may be coupled, either wirelessly or using a cable such as cable 502, to the physician's computer such that software-based programming system 600 may download for review data stored on IPG 300 via external programmer 500. Software-based programming system 600 also may transfer programming data to IPG 300 via external programmer 500 to reprogram stimulation parameters programmed into IPG 300. For example, programming system 600 may be used to program and adjust parameters such as pulse amplitude (voltage or current), pulse width, stimulation rate, stimulation frequency, ramp timing, cycle timing, session timing, and electrode configuration. Programming system 600 also may be configured to upload and store data retrieved from IPG 300 to a remote server for later access by the physician. Programming system 600 may be configured to cause the computer to display an impedance measurement taken at electrode lead 200 and transmitted by IPG 300. The impedance measurement may be used to determine whether the fixation element(s) on electrode lead 200 are in the delivered state or the deployed state, as described in detail below.

Referring now to FIGS. 2A and 2B, an exemplary embodiment of electrode lead 200 is described. Electrode lead 200 contains a plurality of electrodes 204, 206, 208, and 210, disposed at distal end 211 of lead body 202, that are configured to be implanted in or adjacent to tissue, such as nervous tissue, muscle, ligament, and/or joint capsule. Lead body 202 is a suitable length for positioning the electrodes in or adjacent to target tissue while IPG is implanted in a suitable location, e.g., the lower back. For example, lead body 202 may be between about 30 and 80 cm in length, and preferably about 45 or about 65 cm in length. Lead body 202 is also of a suitable diameter for placement, for example, between about 1 and 2 mm in diameter and preferably about 1.3 mm. Electrodes 204, 206, 208, and 210 may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. Electrodes 204, 206, 208, 210 are a suitable length(s) and spaced apart a suitable distance along lead body 202. For example, electrodes 204, 206, 208, 210 may be about 2-5 mm in length, and preferably about 3 mm, and may be spaced apart about 2-6 mm, and preferably about 4 mm. As will also be understood by one of skill in the art, an electrode lead may contain more or fewer than four electrodes.

Also at distal end 211, fixation elements 212 and 213 may be coupled to lead body 202 via fixation ring 216 and fixation elements 214 and 215 may be coupled to lead body 202 via fixation ring 218. Fixation elements 212, 213, 214, 215 are shown in a delivery state in FIG. 2A, wherein fixation elements 212, 213, 214, 215 are positioned adjacent to electrode 210, and are shown in a deployed state in FIG. 2B, wherein fixation elements 212, 213, 214, 215 are spaced apart from electrode 210 and positioned to anchor lead 200 to an anchor site, e.g., muscle.

Fixation elements 212, 213, 214, 215 are configured to collapse inward toward lead body 202 in the delivery state, shown in FIG. 2A, and may contact electrode 210 in the delivery state. In the illustrated embodiment, the longitudinal axis of each fixation element 212, 213, 214, 215, when collapsed, is approximately parallel to the longitudinal axis of lead 200 at distal end 211. In addition, fixation elements 212, 213, 214, 215 may be sized such that the outer surface of each fixation element 212, 213, 214, 215 aligns with the outer surface of fixation rings 216 and 218 to minimize catching of fixation elements 212, 213, 214, 215 when delivered through a sheath. In the delivery state, fixation elements 212, 213, 214, 215 may at least partially cover portions of, or substantially all of, electrode 210. Advantageously, the close proximity of fixation elements 212, 213, 214, 215 to electrode 210 in the delivery state may be utilized to determine whether fixation elements 212, 213, 214, 215 have deployed during delivery because the impedance at electrode 210 is different when fixation elements 212, 213, 214, 215 are deployed as compared to when fixation elements 212, 213, 214, 215 are collapsed adjacent to electrode 210.

Referring now to FIG. 2B, fixation elements 212, 213, 214, 215 are configured to self-expand, e.g., due to retraction of a sheath, in the deployed state. Illustratively, fixation elements 212, 213, 214, 215 are spaced apart from electrode 210 at an angle suitable for anchoring lead 200 to the anchor site. Preferably, in the deployed state, the angle between each fixation element 212, 213, 214, 215 and the longitudinal axis of lead 200 at distal end 211 is between about 10-90 degrees, 20-80 degrees, 25-70 degrees, 30-60 degrees, or 35-55 degrees, and preferably about 45 degrees. As will be readily understood, the angle between each fixation element 212, 213, 214, 215 and the longitudinal axis of lead 200 at distal end 211 need not be the same, and most likely will be different as each fixation element 212, 213, 214, 215 expands individually through tissue.

Fixation elements 212 and 214 are configured to sandwich an anchor site, e.g., muscle, therebetween to secure electrode lead 200 at a target site without damaging the anchor site. Likewise, fixation elements 213 and 215 are configured to sandwich the same or a different anchor site therebetween to secure electrode lead 200 at the target site without damaging that anchor site. Fixation elements 212 and 213 may be angled distally relative to lead body 202, and resist motion in a first direction and prevent, in the case illustrated, insertion of the lead too far, as well as migration distally. Fixation element 212 may be disposed opposite from fixation element 213, as illustrated. Fixation elements 214 and 215 are angled proximally relative to lead body 202 and penetrate through a tissue plane and deploy on the distal side of the tissue immediately adjacent to a target of stimulation. Fixation element 214 may be disposed opposite from fixation element 215, as illustrated. As will be understood by one of skill in the art, an electrode lead may contain more or fewer than four fixation elements.

Fixation elements 212 and 213 are configured to resist motion in the opposite direction relative to fixation elements 214 and 215. This combination prevents migration both proximally and distally, and also in rotation. In the illustrated embodiment, fixation elements 212 and 213 are coupled to lead body 202 between electrode 208 and distal most electrode 210 and fixation elements 214 and 215 are coupled to lead body 202 between distal most electrode 210 and end cap 220.

Fixation elements 212, 213, 214, 215 are preferably made from a nonconductive material, e.g., a nonconductive polymer, and have a generally rectangular cuboid shape, although the disclosure is not limited thereto and other shapes may be utilized such as curved shapes and hooks. The nonconductive material may be used to ensure that impedance at electrode lead 200 will be different between the delivery and the deployed states because the nonconductive material, when contacting or immediately adjacent to electrode 210 in the delivery state, will alter diffusion of energy to/from electrode 210 as compared to when the nonconductive material is spaced apart from electrode 210 in the deployed state. A measurement of the impedance may be used to determine how many fixation elements 212, 213, 214, 215 have deployed, as fixation elements 212, 213, 214, 215 are independently deployable. For example, an impedance measurement within a first range, e.g., between 1501-3500 ohms, may be indicative of fixation elements 212, 213, 214, 215 being in the delivery state and an impedance measurement within a second range, e.g., between 500-1500 ohms, different from the first range, may be indicative of fixation elements 212, 213, 214, 215 being in the deployed state. In addition, an impedance measurement within a third range, e.g., 1200-2500 ohms, different from the first and second ranges, may be indicative of one of fixation elements 212, 213, 214, 215 being in the deployed state while the remaining fixation elements are in the delivery state. Also, an impedance measurement within a fourth range, e.g., 1000-2000 ohms, different from the first, second, and third ranges, may be indicative of two of fixation elements 212, 213, 214, 215 being in the deployed state while the remaining fixation elements are in the delivery state. And an impedance measurement within a fifth range, e.g., 750-1750 ohms, different from the first, second, third, and fourth ranges, may be indicative of three of fixation elements 212, 213, 214, 215 being in the deployed state while the remaining fixation elements are in the delivery state.

The length of and spacing between the fixation elements is defined by the structure around which they are to be placed. In one embodiment, the length of each fixation element is between about 1.5-4 mm and preferably about 2.5 mm and the spacing is between about 2 mm and 10 mm and preferably about 6 mm.

While FIGS. 2A and 2B illustrate fixation elements 212, 213, 214, 215 on lead body 202, it should be understood that other fixation elements may be used to anchor electrode lead 200 at a suitable location including the fixation elements described in U.S. Patent Application Pub. Nos. 2013/0131766 to Crosby and 2013/0338730 to Shiroff, both assigned to the assignee of the present invention, the entire contents of each of which is incorporated herein by reference.

Lead body 202 further may include stylet lumen 222 extending therethrough. Stylet lumen 222 is shaped and sized to permit a stylet to be inserted therein, for example, during delivery of electrode lead 200. In one embodiment, end cap 220 is used to prevent the stylet from extending distally out of stylet lumen 222 beyond end cap 220. In addition, end cap 220 may include a suitable coupling mechanism, e.g., threads, for coupling to the stylet such that the stylet is temporarily locked to end cap 220.

At proximal end 224, electrode lead 200 includes contacts 226, 228, 230, and 232 separated along lead body 202 by spacers 234, 236, 238, 240, and 242. Contacts 226, 228, 230, and 232 may comprise an isodiametric terminal and are electrically coupled to electrodes 204, 206, 208, and 210, respectively, via, for example, individually coated spiral wound wires. A portion of proximal end 224 is configured to be inserted in IPG 300 and set-screw retainer 244 is configured to receive a screw from IPG 300 to secure the portion of electrode lead 200 within IPG 300.

As would be apparent to one of ordinary skill in the art, various electrode locations and configurations would be acceptable, including the possibility of skin surface electrodes. The electrode(s) may be an array of a plurality of electrodes, or may be a simple single electrode where the electrical circuit is completed with an electrode placed elsewhere (not shown) such as a skin surface patch or by the can of an implanted pulse generator. In addition, electrode lead 200 may comprise a wirelessly activated or leadless electrode, such as described in U.S. Pat. No. 8,321,021 to Kisker, such that no lead need be coupled to IPG 300.

With respect to FIG. 3, a generalized schematic diagram of the internal functional components of IPG 300 is now described. IPG 300 is configured to cause the electrodes to stimulate in accordance with programming data stored in the memory of IPG 300. IPG 300 may include programmable controller 318, communication unit 320, power supply 324, electrode switching array 326, system sensors 328, and optional therapeutic circuitry module 330.

Controller 318 is electrically coupled to, and configured to control, the internal functional components of IPG 300. Controller 318 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 318 stores program instructions that, when executed by the processor of controller 318, cause the processor and the functional components of IPG 300 to provide the functionality ascribed to them herein. Controller 318 is configured to be programmable such that programming data is stored in the memory of controller 318 and may be adjusted using external programmer 500 as described in detail in U.S. Patent Pub. No. 2014/0046398 to Sachs, the entire contents of which is incorporated herein by reference. Programming data may include pulse amplitude (voltage or current), pulse width, stimulation rate, stimulation frequency, ramp timing, cycle timing, session timing, and electrode configuration. In accordance with one embodiment, programmable parameters, their ranges, and nominal values are:

| Parameter | Min | Max | Nominal |
| --- | --- | --- | --- |
| Amplitude | 0 mA | 7.0 mA | 1 mA |
| Pulse Width | 25 μs | 500 μs | 200 μs |
| Rate | 1 Hz | 40 Hz | 20 Hz |

-continued

| Parameter | Min | Max | Nominal |
| --- | --- | --- | --- |
| On Ramp | 0 s | 5 s | 2 s |
| Off Ramp | | | |
| Cycle-On | 2 s | 20 s | 10 s |
| Cycle-Off | 20 s | 120 s | 20 s |
| Session | 1 min | 60 min | 30 min |

Controller 318 may be programmable to allow electrical stimulation between any chosen combination of electrodes on the lead, thus providing a simple bipolar configuration. In addition, controller 318 may be programmed to deliver stimulation pulses in a guarded bipolar configuration (more than 1 anode surrounding a central cathode) or the housing of IPG 300 may be programmed as the anode, enabling unipolar stimulation from any of the electrodes. IPG 300 may have two separate channels to facilitate bilateral stimulation and the electrode configuration, e.g., combination of positive and negative electrodes, may be programmed independently for each channel.

As will be appreciated by one of ordinary skill in the art, while IPG 300 is illustratively implantable, a pulse generator may be disposed external to a body of a patient on a temporary or permanent basis without departing from the scope of the present invention. For example, an external stimulator may be coupled to the electrodes wirelessly.

Controller 318 further may be programmed with a routine to calculate the impedance at electrode lead 200. For example, controller 318 may direct power supply 324 to send an electrical signal to one or more electrodes which emit electrical power. One or more other electrodes receive the emitted electrical power and send a received signal to controller 318 that runs the routine to calculate impedance based on the sent signal and the received signal. The impedance measurement may be used to determine whether one or more of the fixation elements coupled to the electrode lead body are in a delivery state or a deployed state. In one embodiment, controller 318 directs electrode 210 to emit energy such that electrode 204, 206, or 208 receives a portion of the emitted energy and sends a received signal to controller 318. Also, controller 318 may direct electrode 204, 206, or 208 to emit energy such that electrode 210 receives a portion of the emitted energy and sends a received signal to controller 318. Controller 318 runs the routine to calculate impedance based on the signal having data indicative of emitted energy and the signal having data indicative of received energy to determine an impedance measurement. Advantageously, the proximity of the fixation element(s) to the electrode(s) will change the impedance measured at the electrode(s) as the resistance of the electrical energy traveling between electrodes increases as the angle between the fixation element(s) and the electrode(s) decreases. For example, the resistance of electrical energy traveling between electrode 210 and electrode 204, 206, or 208 may be higher in the delivery state than in the deployed state.

Controller 318 causes communication unit 320 to transmit a signal indicative of the impedance measurement to the external computer running software 600, e.g., via external programmer 500. A physician may review the impedance measurement on software 600 to determine whether one or more fixation elements are in the deployed or the delivery state. If the physician determines that one or more of the fixation elements are in the delivery state after retraction of a sheath, the physician may adjust the lead in an attempt to cause the non-deployed fixation element(s) to deploy. Then, the physician may request a second impedance measurement using software 600. The external computer transmits the command, e.g., via external programmer 500, to IPG 300 and controller 318 repeats the steps to calculate impedance. Controller 318 then directs communication unit 320 to transmit a second signal indicative of the second impedance measurement to the external computer running software 600, e.g., via external programmer 500. The physician may determine whether one or more fixation elements have deployed based on the second impedance measurement. The physician may continue to adjust the lead and request impedance measurements as necessary until the physician is satisfied that the fixation elements have deployed.

Controller 318 is coupled to communication unit 320 having circuitry configured to communicate with activator 400 and the external computer, e.g., via external programmer 500. Communication unit 320 permits transmission of stimulation commands, and optionally power, between IPG 300 and activator 400 such that IPG 300 may be powered, programmed, and/or controlled by activator 400. For example, controller 318 may start or stop a treatment session or to conduct an impedance assessment responsive to stimulation commands received from a corresponding communication unit (e.g., an inductive unit having a telemetry system and coil and/or a RF unit having a transceiver and antenna) of activator 400. Communication unit 320 further permits transmission of programming data, and optionally power, between IPG 300 and external programmer 500 such that IPG 300 may be powered, programmed, and/or controlled by software-based programming system 600 via external programmer 500. For example, controller 318 may direct changes to at least one of pulse amplitude (voltage or current), pulse width, stimulation rate, stimulation frequency, ramp timing, cycle timing, session timing, and electrode configuration and to conduct an impedance assessment responsive to programming data received from a corresponding communication unit (e.g., an inductive unit having a telemetry system and coil and/or a RF unit having a transceiver and antenna) of external programmer 500.

Communication unit 320 may include a telemetry system electrically coupled to an inductive coil. The technology for telemetry systems and coils is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer. Alternatively, the coil may be used to transmit power only, and separate radio frequency transmitters may be provided in IPG 300 activator 400, and/or external programmer 500 for establishing bidirectional or unidirectional data communication.

Communication unit 320 also may include (with or without the telemetry system and coil) a communications circuit employing a transceiver coupled to an antenna 334 (which may be inside or external to the hermetic housing). The transceiver preferably comprises a radio frequency (RF) transceiver and is configured for bi-directional communications via the antenna with a similar transceiver circuit disposed in activator 400 and/or external programmer 500. For example, the transceiver may receive stimulation commands from activator 400 and programming data from software-based programming system 600 via external programmer 500. Controller 318 may direct changes to at least one of pulse amplitude (voltage or current), pulse width, stimulation rate, stimulation frequency, ramp timing, cycle timing, session timing, and electrode configuration, including commands to start or stop a treatment session or to conduct impedance assessment, responsive to programming data and/or stimulation commands received from a corresponding transceiver and antenna of activator 400 and/or external programmer 500 via the antenna and the transceiver of communication unit 320. The transceiver also may include a low power mode of operation, such that it periodically awakens to listen for incoming messages and responds only to those messages including the unique device identifier assigned to that IPG. In addition, the transceiver may employ an encryption routine to ensure that messages sent from, or received by, IPG 300 cannot be intercepted or forged. Communication unit 320 may include a wireless chipset, e.g., WiFi, Bluetooth, cellular, thereby enabling IPG 300 to communicate wirelessly with activator 400, external programmer 500, and/or the external computer running software 600.

Power supply 324 powers the electrical components of IPG 300, and may comprise a primary cell or battery, a secondary (rechargeable) cell or battery or a combination of both. Alternatively, power supply 324 may not include a cell or battery, but instead comprise a capacitor that stores energy transmitted through the skin via a Transcutaneous Energy Transmission System (TETs), e.g., by inductive coupling. In a preferred embodiment, power supply 324 comprises a lithium ion battery.

Controller 318 further may be coupled to electrode switching array 326 so that any subset of electrodes of the electrode leads may be selectably coupled to therapeutic circuitry module 330, described in detail below. In this way, an appropriate electrode set may be chosen from the entire selection of electrodes implanted in the patient's body to achieve a desired therapeutic effect. Electrode switching array 326 preferably operates at high speed, thereby allowing successive stimulation pulses to be applied to different electrode combinations.

System sensors 328 may comprise one or more sensors that monitor operation of the systems of IPG 300, and log data relating to system operation as well as system faults, which may be stored in a log for later readout using software-based programming system 600. In one embodiment, system sensors 328 include a magnetic sensor configured to sense a magnetic field and to transmit a signal to controller 318 based on the sensed magnetic field such that the controller starts or stops a treatment session. In another embodiment, system sensors 328 include one or more sensors configured to sense muscle contraction and to generate a sensor signal based on the muscle contraction. Controller 318 is configured to receive the sensor signal from system sensors 328 and to adjust the stimulation parameters based on the sensor signal. In one embodiment, system sensors 328 sense an increase or decrease in muscle movement and controller 318 increases or decreases the stimulation frequency to maintain smooth and continuous muscle contraction.

In one embodiment, sensors 328 may include an accelerometer that senses acceleration of a muscle caused by muscle contraction. The accelerometer may be a 1-, 2- or 3-axis analog or digital accelerometer that determines whether the patient is active or asleep or senses overall activity of the patient, which may be a surrogate measure for clinical parameters (e.g., more activity implies less pain), and/or a heart rate or breathing rate (minute ventilation) monitor, e.g., which may be obtained using one or more of the electrodes disposed on the electrode leads. The accelerometer may be used to determine the orientation of IPG 300, and by inference the orientation of the patient, at any time. For example, after implantation, software-based programming system 600 may be used to take a reading from the implant, e.g., when the patient is lying prone, to calibrate the orientation of the accelerometer. If the patient is instructed to lie prone during therapy delivery, then the accelerometer may be programmed to record the orientation of the patient during stimulation, thus providing information on patient compliance. In other embodiments, system sensors 328 may include a pressure sensor, a movement sensor, and/or a strain gauge configured to sense muscle contraction and to generate a sensor signal based on the muscle contraction, and in a further embodiment, various combinations of at least one of an accelerometer, a pressure sensor, a movement sensor, and/or a strain gauge are included.

Sensors 328 may also include, for example, a humidity sensor to measure moisture within housing 304, which may provide information relating to the state of the electronic components, or a temperature sensor, e.g., for measuring battery temperature during charging to ensure safe operation of the battery. Data from the system sensors may be logged by controller 318 and stored in nonvolatile memory for later transmission to software-based programming system 600 via external programmer 500.

As will be appreciated by one of ordinary skill in the art, system sensors 328 may be placed in a variety of locations including within housing 302, within or adjacent to the tissue that is stimulated, and/or in proximity to the muscle to be contracted and connected via a separate lead to IPG 300. In other embodiments, sensors 324 may be integrated into one or more of the leads used for stimulation or may be an independent sensor(s) operatively coupled to IPG 300 using, for example, radio frequency (RF) signals for transmitting and receiving data.

Controller 318 also may be coupled to optional therapeutic circuitry module 330 that provides any of a number of complimentary therapeutic stimulation, analgesic, feedback or ablation treatment modalities as described in detail below. IPG 300 illustratively includes one therapeutic circuitry module 330, although additional circuitry modules may be employed in a particular embodiment depending upon its intended application, as described in U.S. Patent Application Publication No. 2011/0224665 to Crosby, assigned to the assignee of the present invention, the entire contents of which is incorporated herein by reference. Therapeutic circuitry module 330 may be configured to provide different types of stimulation, either to induce muscle contractions or to block pain signals in afferent nerve fibers; to monitor muscle contractions induced by stimulation and adjust the applied stimulation regime as needed to obtain a desired result; or to selectively and intermittently ablate nerve fibers to control pain and thereby facilitate muscle rehabilitation.

Figure 4:
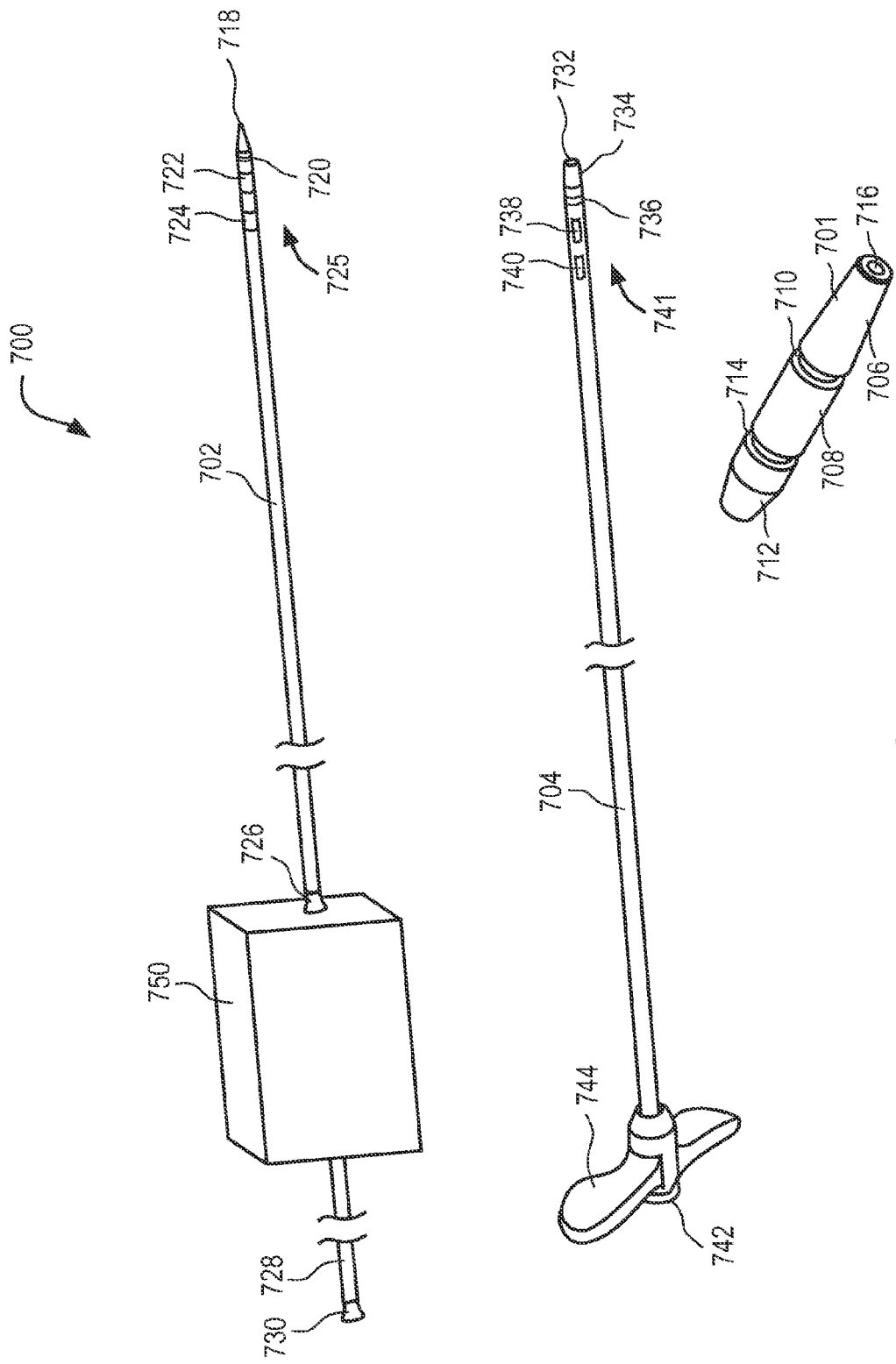
FIG. 4 shows an exemplary kit for delivering the electrode lead of the stimulator system of FIG. 1.

Referring now to FIG. 4, kit 700 for delivering electrode lead 200 is described, including suture sleeve 701, needle electrode 702, and sheath 704. In FIG. 4, components of the kit are not depicted to scale on either a relative or absolute basis. Suture sleeve 701 illustratively includes first end section 706, middle section 708 separated from first end section by first groove 710, second end section 712 separated from middle section 708 by second groove 714, and sleeve lumen 716. First and second end sections 706 and 712 may have truncated conical portions as shown. First and second grooves 710 and 714 are sized and shaped to accept sutures such that suture sleeve 701 may be secured to tissue, e.g., superficial fascia, using the sutures. Sleeve lumen 716 is sized such that electrode lead 200 may be inserted therethrough.

Needle electrode 702 may include distal tip 718, radiopaque marker 720, electrodes 722, 724 disposed near distal tip 718, and connector 726. Distal tip 718, radiopaque marker 720, and electrodes 722, 724 are located at distal end 725 of needle electrode 702. Distal tip 718 is shaped with a needle point to facilitate insertion of needle electrode 702 through tissue to the target site. Alternatively, distal tip 718 may have a blunt end to minimize tissue damage during insertion and to separate anatomical structures along naturally occurring tissue planes. Radiopaque marker 720 is configured to permit visualization of needle electrode 702 under fluoroscopic, acoustic, anatomic, or CT guidance during insertion. Electrodes 722, 724 are configured to emit energy to stimulate tissue. As will be understood by one of skill in the art, a needle electrode may contain more or fewer than two electrodes and more than one radiopaque marker.

Needle electrode 702 may be coupled to processor housing 750, e.g., via connector 726. Alternatively, needle electrode 702 may be coupled directly to an external computer such as the computer running software 600, e.g., via connector 726. Processor housing 750 houses circuitry configured to cause electrodes 722, 724 emit energy responsive to user input at the housing itself or at the computer running software 600. Processor housing 750 may be coupled to a computer, such as the computer running software 600, via cable 728 and connector 730.

Sheath 704 may include sheath lumen 732, distal tip 734, radiopaque marker 736, windows 738, 740 near distal tip 734, coupling portion 742, and handle 744. Distal tip 734, radiopaque marker 736, and windows 738, 740 are located at distal end 741 of sheath 704. Sheath lumen 732 extends through sheath 704 and is shaped and sized to permit needle electrode 702 to slide therethrough. Distal tip 734 is beveled to ease introduction through tissue. Radiopaque marker 736 is configured to permit visualization of sheath 704 under fluoroscopic, acoustic, anatomic, or CT guidance during insertion. Windows are configured to permit energy emitted from electrodes disposed within sheath 704 to travel therethrough while the electrodes remain within the sheath. Accordingly, the electrodes, e.g., electrodes on electrode lead 200 or needle electrode 702, need not extend out the distal end of sheath 704 to stimulate tissue. Advantageously, proper positioning of the electrodes may be verified while the electrodes remain within sheath 704 minimizing the likelihood of needing to adjust electrode position after deployment, including deployment of a fixation element(s). Coupling portion 742, illustratively a male end with threads, is configured to be coupled to a portion of needle electrode 702. Handle 744 is sized and shaped to permit a physician to comfortably hold sheath 704. As will be understood by one of skill in the art, a sheath may contain more or fewer than two windows and more than one radiopaque marker.

Figure 5:
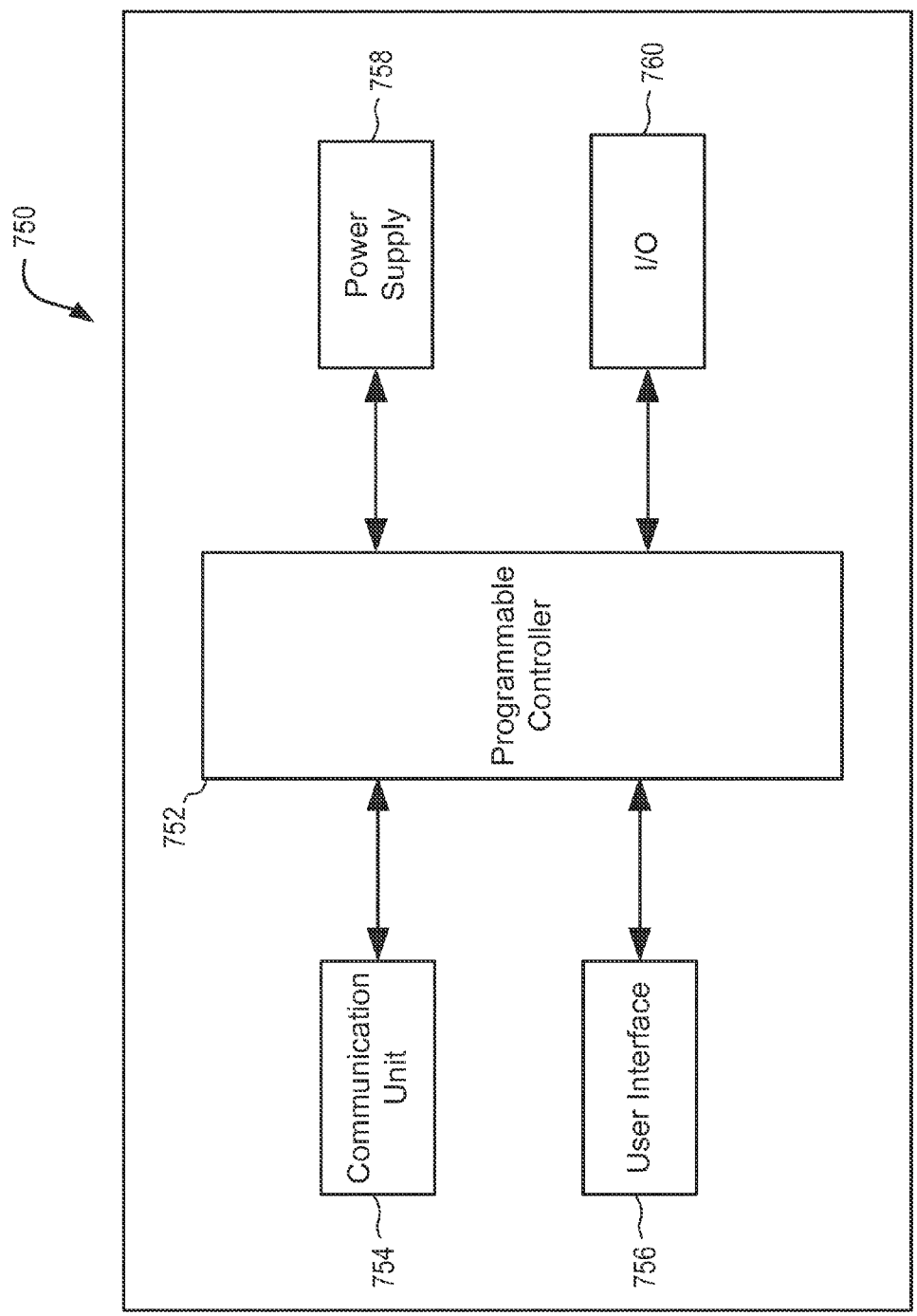
FIG. 5 shows a generalized block diagram of an exemplary circuitry housing that may be used together with the needle electrode of the kit of FIG. 4.

With respect to FIG. 5, a generalized schematic diagram of the internal functional components of processor housing 750 is now described. Processor housing 750 may include programmable controller 752, communication unit 754, user interface 756, power supply 758, and input and output circuitry (I/O) 760.

Controller 752 is electrically coupled to, and configured to control, the internal functional components of processor housing 750. Controller 752 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 752 may store program instructions that, when executed by the processor of controller 752, cause the processor and the functional components of processor housing 750 to provide the functionality ascribed to them herein. Controller 752 is configured to be programmable. For example, controller 752 may store and adjust stimulation parameters, e.g., pulse amplitude (voltage or current), pulse width, stimulation rate, stimulation frequency, ramp timing, cycle timing, session timing, and electrode configuration responsive to user input received at user interface 756 or at an external computer such as the computer running software 600.

Controller 752 may be coupled to communication unit 754, which is configured to communicate with an external computer, such as the computer running software 600. Communication unit 754 may include a wireless chipset, e.g., WiFi, Bluetooth, cellular, thereby enabling processor housing 750 to communicate wirelessly with external programmer 500 and/or the external computer running software 600.

User interface 756 is configured to receive user input and to display information to the user. User interface 756 may include buttons, LEDs, a display, a touch screen, a keypad, a microphone, a speaker, a trackball, or the like for receiving user input and/or displaying information to the user. For example, user interface 756 may display current stimulation parameters and permit a user to adjust the stimulation parameters. User interface 756 also may permit a user to cause one or more electrodes 722, 724 to emit energy.

Power supply 758 powers the electrical components of processor housing 750, and may comprise a primary cell or battery, a secondary (rechargeable) cell or battery or a combination of both. Alternatively, power supply 758 may be a port to allow processor housing 750 to be plugged into a conventional wall socket for powering components. Controller 752 may direct power supply 758 to send an electrical signal to one or more electrodes 722, 724 which emit electrical energy at the stimulation parameters programmed in controller 752.

Input and output circuitry (I/O) 760 may include ports for data communication such as wired communication with a computer and/or ports for receiving removable memory, e.g., SD card, upon which program instructions or data related to processor housing 750 use may be stored. In one embodiment, I/O 760 includes a port for connection to needle electrode 702 via connector 726 and another port for accepting cable 728 which may be connected to an external computer.

Figure 6A:
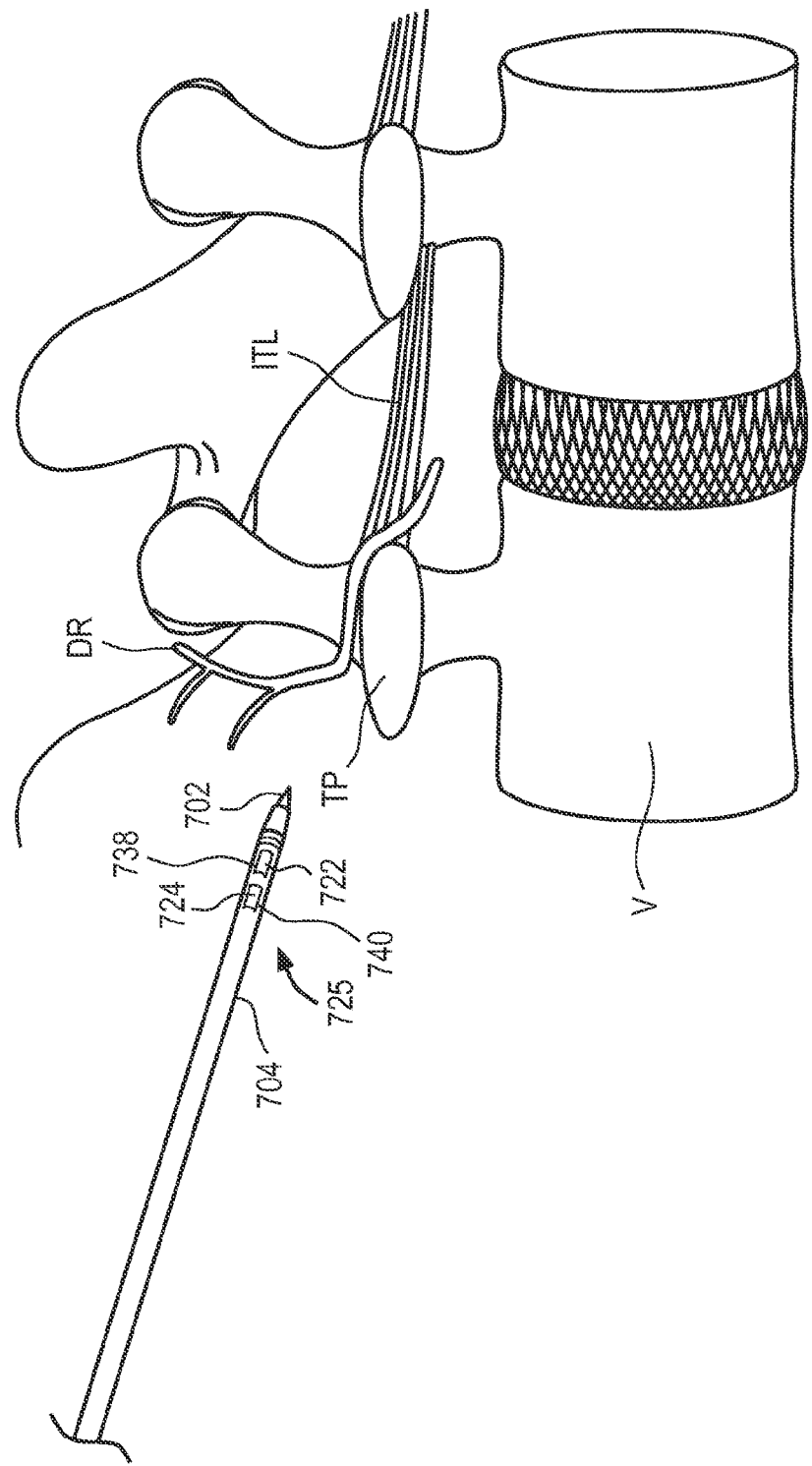

Referring now to FIGS. 6A to 6F, an exemplary method for implanting an electrode lead is described. Using fluoroscopy, acoustic, anatomic, or CT guidance, needle electrode 702 and sheath 704 are inserted transcutaneously and transmuscularly to a target site, e.g., in or adjacent to tissue associated with control of the lumbar spine. Preferably, distal end 725 of needle electrode 702 is positioned in or adjacent to the tissue, as shown in FIG. 6A. Such tissue may include nervous tissue, muscle, ligament, and/or joint capsule. In one embodiment, muscle includes skeletal muscle such as the multifidus, transverse abdominus, quadratus lumborum, psoas major, internus abdominus, obliquus externus abdominus, and erector spinae muscles and nervous tissue includes a peripheral nerve that innervates skeletal muscle. In a preferred embodiment, nervous tissue comprises the dorsal ramus nerve, or fascicles thereof, that innervate the multifidus muscle. Preferably, needle electrode 702 is disposed within sheath lumen 732 prior to insertion such that needle electrode 702 and sheath 704 are inserted together. Advantageously, a guidewire need not be delivered (i) prior to insertion of needle electrode 702 or sheath 704, (ii) through needle electrode 702 or sheath 704 during insertion, or (iii) through needle electrode 702 or sheath 704 after insertion.

FIGS. 6A-6F depict a lateral projection of a segment of a typical human lumbar spine shown having a vertebral body V, transverse process TP, inter-transverse ligament ITL, and a dorsal ramus DR. In FIG. 6A, sheath 704 having needle electrode 702 disposed therethrough, is positioned adjacent to the target site, illustratively, the medial branch of the dorsal ramus DR nerve that innervates the multifidus muscle. Distal tip 718 of needle electrode 702 may extend out of the distal end of sheath 704 to facilitate insertion through tissue. In one embodiment, electrodes of the electrode lead are positioned to stimulate the medial branch of the dorsal ramus that exits between the L2 and L3 lumbar segments and passes over the transverse process of the L3 vertebra, thereby eliciting contraction of fascicles of the lumbar multifidus at the L3, L4, L5 and S1 segments and in some patients also at the L2 segment.

Next, needle electrode 702 stimulates the tissue. Preferably, electrode 722 and/or electrode 724 stimulates the tissue at the stimulation parameters defined at processor housing 750. In an embodiment where sheath 704 has windows 738, 740, electrodes 722, 724 of needle electrode 702 emit energy through windows 738, 740 while electrodes 722, 724 remain within sheath 704. Preferably, windows 738, 740 are sized and spaced with the same or similar dimensions to the length and spacing of electrodes 722, 724 of needle electrode 702 and/or electrodes 204, 206, 208, 210 of electrode lead 200. In this way, the electrodes are more likely to be aligned with the windows while disposed within the patient. In addition, radiopaque markers 720, 736 of needle electrode 702, sheath 704, respectively, may be positioned such that electrodes 722, 724 align within windows 738, 740, respectively, when radiopaque markers 720, 736 are aligned. Similarly, a radiopaque marker(s) may be disposed on electrode lead 200 to facilitate alignment of electrodes 204, 206, 208, 210 within the windows of the sheath. In one embodiment, one or more fixation elements 212, 213, 214, 215 has a radiopaque marker(s) to assist in visualization under fluoroscopic, acoustic, anatomic, or CT guidance to determine whether one or more of the fixation elements are in the delivery state or the deployed state.

Figure 6B:
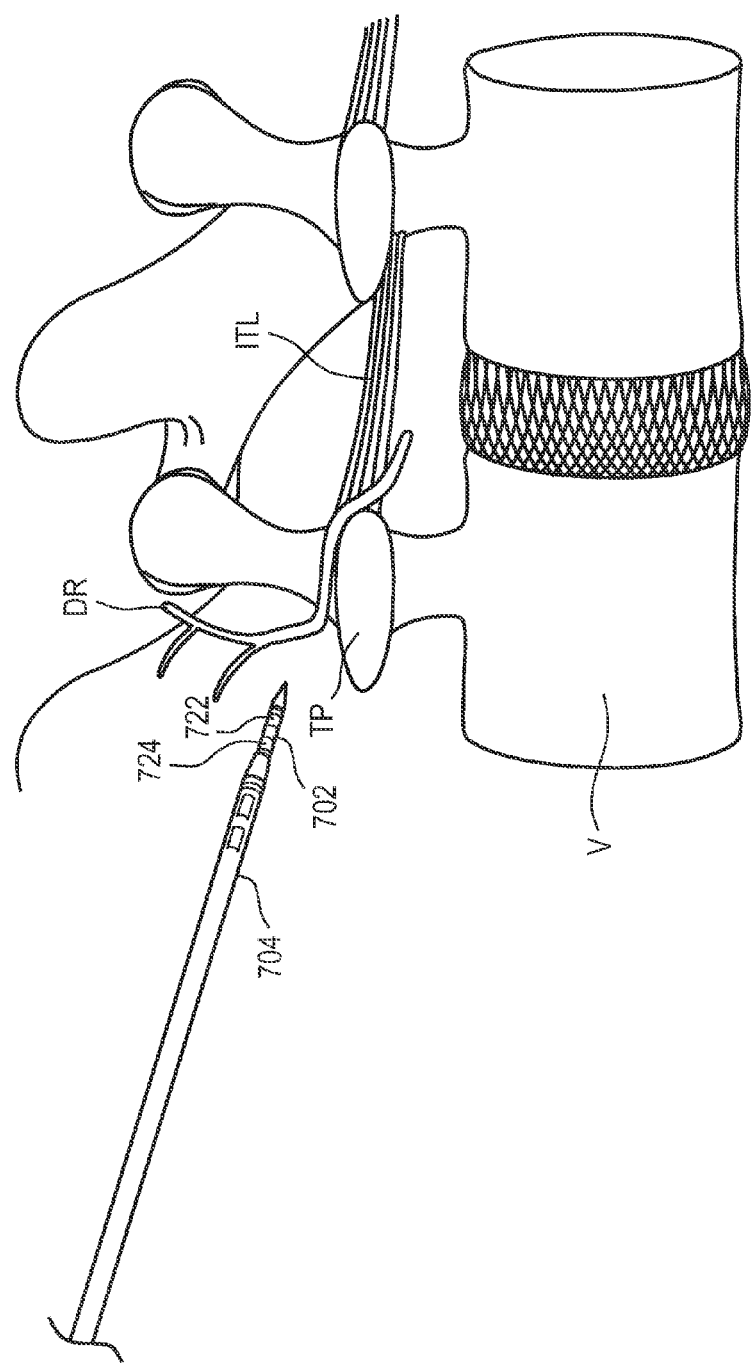

Alternatively, or additionally, distal end 725 of needle electrode 702 may be moved distally out of the distal end of sheath 704 while maintaining position of sheath 704 (or sheath 704 moved proximally, e.g., using handle 744, while maintaining position of needle electrode 702), thereby exposing electrodes 722, 724, as shown in FIG. 6B. Such a step may be useful in embodiments where the sheath does not have windows. Once exposed, needle electrode 702 stimulates the tissue. Preferably, electrode 722 and/or electrode 724 stimulates the tissue at the stimulation parameters defined at processor housing 750.

By stimulating the tissue, proper placement of needle electrode 702 and sheath 704 may be verified. For example, using fluoroscopy, acoustic, anatomic, or CT imaging, a physician may verify that the target muscle contracts responsive to the stimulation. If the target muscle does not contract, or does not contract in a suitable manner, the physician may adjust placement of needle electrode 702 and/or sheath 704, e.g., by moving needle electrode 702 and/or sheath 704 proximally or distally. The physician may continue to make adjustments until suitable placement of needle electrode 702 and/or sheath 704 has been verified.

Figure 6C:
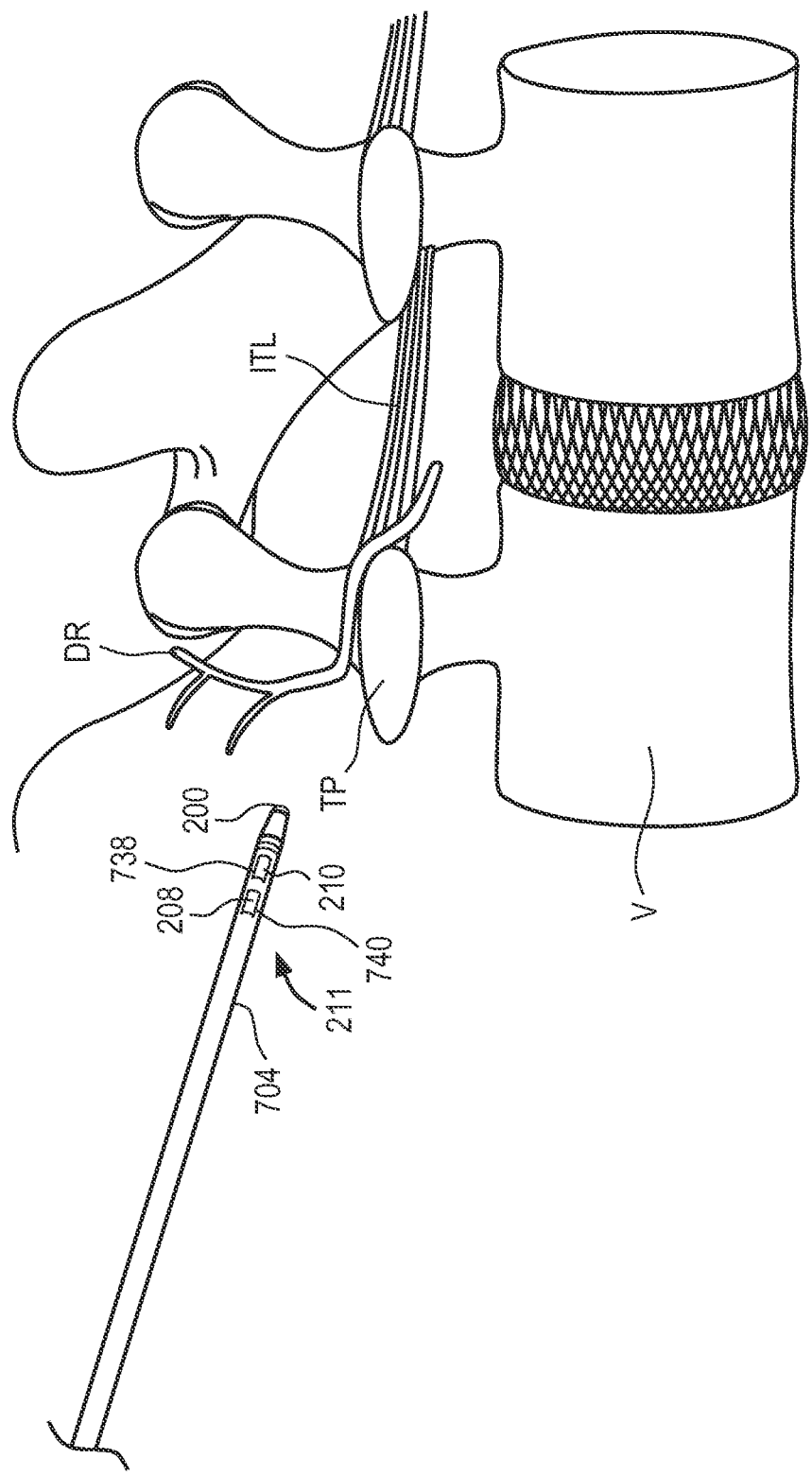

After verification, needle electrode 702 is removed from sheath 704 while maintaining position of sheath 704 at the target site. Using fluoroscopy, acoustic, anatomic, or CT guidance, electrode lead 200 is inserted through sheath lumen 732 of sheath 704 to position electrodes 204, 206, 208, 210 at the target site, as shown in FIG. 6C. As described above, a radiopaque marker on electrode lead 200 may be aligned with radiopaque marker 736 of sheath 704 to ensure that distal end 211 of electrode lead 200 is at distal end 741 of sheath 704, and optionally, that the electrodes of electrode lead 200 are aligned within respective windows of sheath 704. Advantageously, a guidewire need not be delivered (i) prior to insertion of electrode lead 200, (ii) through electrode lead 200 during insertion, or (iii) through electrode lead 200 after insertion.

A stylet may be inserted within the stylet lumen of electrode lead 200 to provide additional stiffness to electrode lead 200 to ease passage of electrode lead 200 through sheath 704. The stylet may be a commercially available stylet such as a locking stylet available from Cook Group Incorporated of Bloomington, Ind.

Next, electrode lead 200 stimulates the tissue. Preferably, electrode 204, 206, 208 and/or electrode 210 stimulates the tissue at the stimulation parameters defined at a pulse generator, such as IPG 300, coupled to the electrodes. In an embodiment where sheath 704 has windows 738, 740, electrodes 210, 208 of electrode lead 200 emit energy through windows 738, 740, respectively, while electrodes 210, 208 remain within sheath 704. As will be understood by one of skill in the art, a sheath may contain more or fewer than two windows. For example, sheath 704 may have four windows sized and shaped to align with electrodes 204, 206, 208, 210 of electrode lead. Advantageously, proper positioning of the electrodes may be verified while the electrodes remain within sheath 704 minimizing the likelihood of needing to adjust electrode position after deployment, including deployment of a fixation element(s) on electrode lead 200.

Figure 6E:
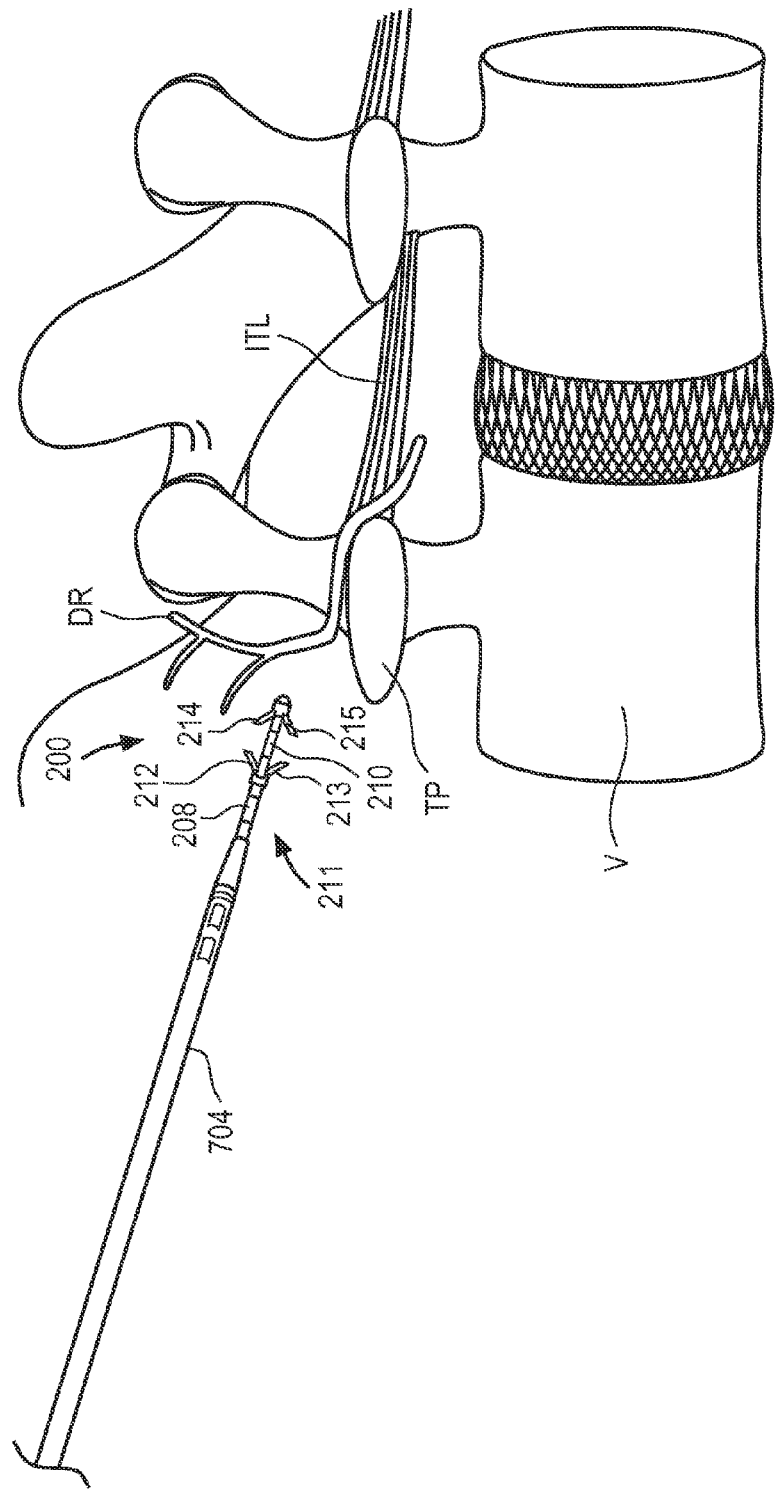

Alternatively, or additionally, distal end 211 of electrode lead 200 may be moved distally out of the distal end of sheath 704 while maintaining position of sheath 704 (or sheath 704 moved proximally, e.g., using handle 744, while maintaining position of electrode lead 200), thereby exposing one or more electrodes 204, 206, 208, and/or 210, as shown in FIGS. 6D and 6E. Such a step may be useful in embodiments where the sheath does not have windows. After electrode exposure, electrode lead 200 stimulates the tissue. Preferably, electrode 204, 206, 208 and/or electrode 210 stimulates the tissue at the stimulation parameters defined at a pulse generator, such as IPG 300, coupled to the electrodes.

By stimulating the tissue, proper placement of electrode lead 200 may be verified, and specifically placement of electrodes 204, 206, 208, 210 at distal end 211 may be verified. For example, using fluoroscopy, acoustic, anatomic, or CT imaging, a physician may verify that the target muscle contracts responsive to the stimulation. If the target muscle does not contract, or does not contract in a suitable manner, the physician may adjust placement of electrode lead 200 and/or sheath 704, e.g., by moving electrode lead 200 and/or sheath 704 proximally or distally. The physician may continue to make adjustments until suitable placement of electrode lead 200 has been verified.

Preferably, fixation elements 212, 213, 214, 215 individually transition from a collapsed, delivery state within sheath 704 to an expanded, deployed state, shown in FIG. 6E, as the respective fixation element is exposed out of the distal end of sheath 704. The fixation elements sandwich an anchor site, e.g., muscle, therebetween without damaging the anchor site in the expanded state to fix electrode lead 200 at the target site. However, it is contemplated that one or more fixation elements 212, 213, 214, 215 may not expand to the deployed state, as shown in FIG. 6D.

A method for verifying deployment of one or more fixation elements is now described. After implantation of electrode lead 200 at the target site as described above, electrode lead 200 stimulates the tissue. Preferably, electrode 204, 206, 208 and/or electrode 210 stimulates the tissue at the stimulation parameters responsive to a signal sent by a pulse generator, such as IPG 300, coupled to the electrodes. One or more other electrodes receive the emitted electrical power and send a received signal to the controller of the pulse generator that runs the routine to calculate impedance based on the sent signal and the received signal. The impedance measurement may be used to determine whether one or more fixation elements 212, 213, 214, 215 are in a delivery state or a deployed state. In one embodiment, the pulse generator directs electrode 210 to emit energy such that electrode 204, 206, or 208 receives a portion of the emitted energy and sends a received signal to the pulse generator. Also, the pulse generator may direct electrode 204, 206, or 208 to emit energy such that electrode 210 receives a portion of the emitted energy and sends a received signal to the pulse generator. The pulse generator runs the routine to calculate impedance based on the signal having data indicative of emitted energy and the signal having data indicative of received energy to determine an impedance measurement. Advantageously, the proximity of the fixation element(s) to the electrode(s) will change the impedance measured at the electrode(s) as the resistance of the electrical energy traveling between electrodes increases as the angle between the fixation element(s) and the electrode(s) decreases. For example, the resistance of electrical energy traveling between electrode 210 and electrode 204, 206, or 208 may be higher in the delivery state than in the deployed state.

The pulse generator transmits a signal indicative of the impedance measurement to the external computer running software 600, e.g., via external programmer 500. A physician may review the impedance measurement on software 600 to determine whether one or more fixation elements 212, 213, 214, 215 are in the deployed or the delivery state. If the physician determines that one or more fixation elements 212, 213, 214, 215 are in the delivery state after retraction of a sheath (as is shown in FIG. 6D), the physician may adjust electrode lead 200 in an attempt to cause the non-deployed fixation element(s) to deploy, e.g., move electrode lead 200 proximally and/or distally. Then, the physician may request a second impedance measurement using software 600. The external computer transmits the command, e.g., via external programmer 500, to the pulse generator which repeats the steps to calculate impedance. The pulse generator then transmits a second signal indicative of the second impedance measurement to the external computer running software 600, e.g., via external programmer 500. The physician may determine whether one or more fixation elements 212, 213, 214, 215 have deployed based on the second impedance measurement. The physician may continue to adjust electrode lead 200 and request impedance measurements as necessary until the physician is satisfied that fixation elements 212, 213, 214, 215 have all deployed.

In one embodiment, software 600 is configured to determine if the fixation element(s) is deployed and, preferably, how many fixation elements have deployed. For example, software 600 may process the impedance measurement to determine whether a fixation element(s) is deployed using a lookup table having stored impedance value ranges corresponding to the number of fixation elements deployed. Software 600 may cause the computer running software 600 to display a message reflecting the number of fixation elements deployed and/or reflecting suitable/unsuitable deployment of the fixation elements.

Figure 6F:
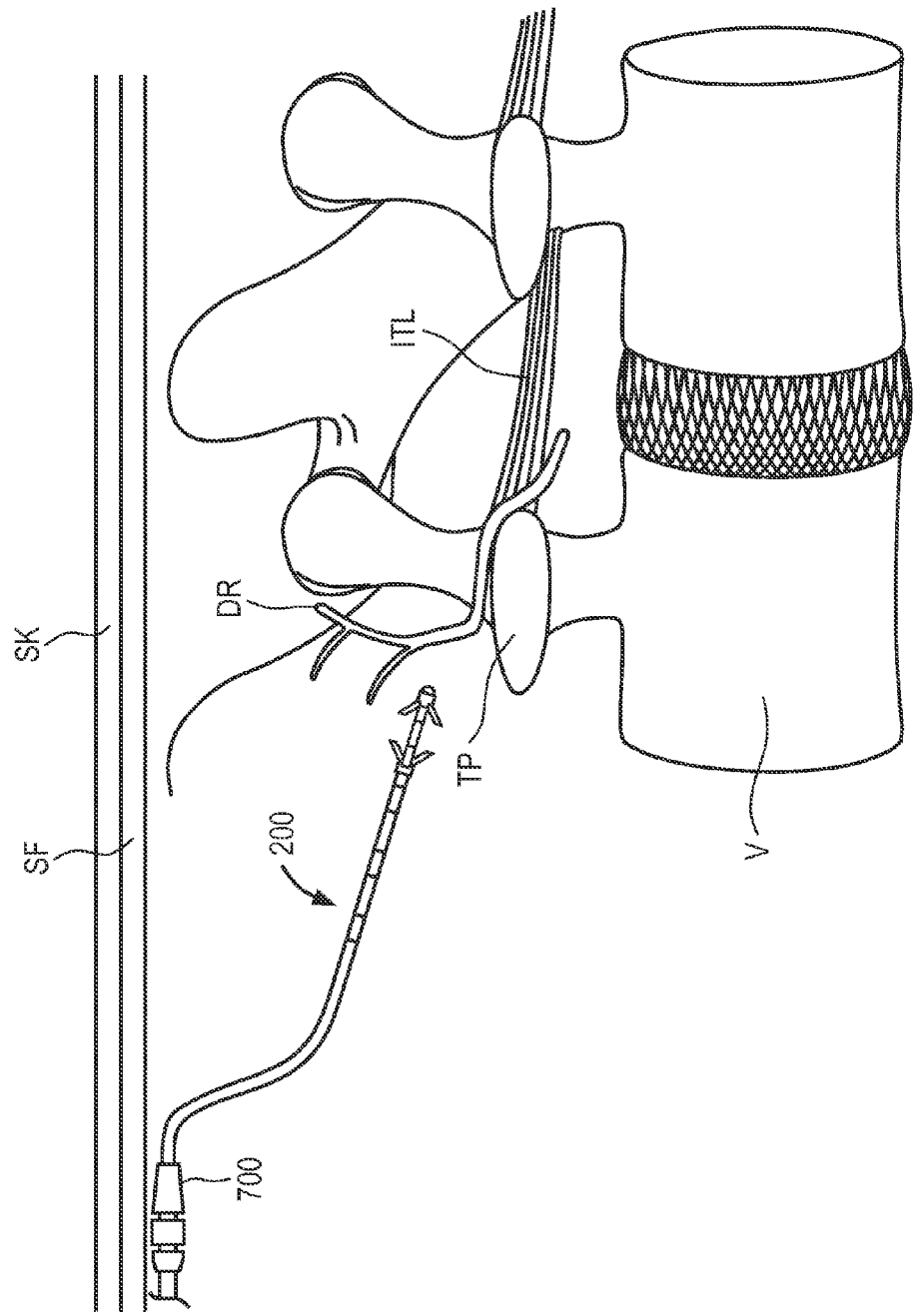

After verification that electrode lead 200 is suitably positioned within the patient at the target site, and preferably after verification that the fixation element(s) is deployed, sheath 704 is moved proximally off the proximal end of electrode lead 200 and suture sleeve 701 is placed over the proximal end of electrode lead 200 and moved distally, as illustrated in FIG. 6F. When suture sleeve 701 is positioned adjacent to the superficial fascia SF beneath skin SK, sutures are sewn into the first and second grooves of suture sleeve 701 so as to secure suture sleeve 701 to the superficial fascia SF.

Finally, the IPG is coupled to the proximal end of electrode lead 200 and implanted within the lower back of the patient.

Exemplary stimulation parameters are now described. Preferably, such stimulation parameters are selected and programmed to induce contraction of muscle to restore neural control and rehabilitate muscle associated with control of the spine, thereby improving lumbar spine stability and reducing back pain. As used in this specification, "to restore muscle function" means to restore an observable degree of muscle function as recognized by existing measures of patient assessment, such as the Oswestry Disability Index ("ODI") as described in Lauridsen et al., *Responsiveness and minimal clinically important difference for pain and disability instruments in low back pain patients*, BMC Musculoskeletal Disorders, 7: 82-97 (2006), the European Quality of Life Assessment 5D ("EQ-5D") as described in Brazier et al., *A comparison of the EQ-5D and SF-6D across seven patient groups*, Health Econ. 13: 873-884 (2004), or a Visual Analogue Scale ("VAS") as described in Hagg et al., *The clinical importance of changes in outcome scores after treatment for chronic low back pain*, Eur Spine J 12: 12-20 (2003). In accordance with one aspect of the present invention, "to restore muscle function" means to observe at least a 15% improvement in one of the foregoing assessment scores within 30-60 days of initiation of treatment. As described above, the stimulation parameters may be programmed into the IPG, may be adjusted in the IPG responsive to (i) stimulation commands transferred from the activator or (ii) programming data transferred from the external programmer.

The stimulation parameters include, for example, pulse amplitude (voltage or current), pulse width, stimulation rate, stimulation frequency, ramp timing, cycle timing, session timing, and electrode configuration, including commands to start or stop a treatment session. In one embodiment, pulse amplitude is programmed to be adjustable between 0 and 7 mA. In a preferred embodiment, pulse amplitude is programmed to be between about 2-5 mA, 2.5-4.5 mA, or 3-4 mA, and preferably about 3.5 mA. In one embodiment, pulse width is programmed to be adjustable between 25 and 500 μs. In a preferred embodiment, pulse width is programmed to be between about 100-400 μs, 150-350 μs, or 200-300 μs, and preferably about 350 μs. In one embodiment, stimulation rate is programmed to be adjustable between 1 and 40 Hz. In a preferred embodiment, stimulation rate is programmed to be between about 5-35 Hz, 10-30 Hz, or 15-20 Hz, and preferably about 20 Hz. In one embodiment, on ramp timing is programmed to be adjustable between 0 and 5 s. In a preferred embodiment, on ramp timing is programmed to be between about 0.5-4.5 s, 1-4 s, 1.5-3.5 s, or 2-3 s, and preferably about 2.5 s. In one embodiment, off ramp timing is programmed to be adjustable between 0 and 5 s. In a preferred embodiment, off ramp timing is programmed to be between about 0.5-4.5 s, 1-4 s, 1.5-3.5 s, or 2-3 s, and preferably about 2.5 s. In one embodiment, cycle-on timing is programmed to be adjustable between 2 and 20 s. In a preferred embodiment, cycle-on timing is programmed to be between about 4-18 s, 6-16 s, 8-14 s, 9-13 s, or 10-12 s and preferably about 10 s. In one embodiment, cycle-off timing is programmed to be adjustable between 20 and 120 s. In a preferred embodiment, cycle-off timing is programmed to be between about 30-110 s, 40-100 s, 50-90 s, 55-85 s, 60-80 s, or 65-75 s and preferably about 70 s. In one embodiment, session timing is programmed to be adjustable between 1 and 60 min. In a preferred embodiment, session timing is programmed to be between about 5-55 min, 10-50 min, 15-45 min, 20-40 min, or 25-35 min, and preferably about 30 min.

Figure 7:
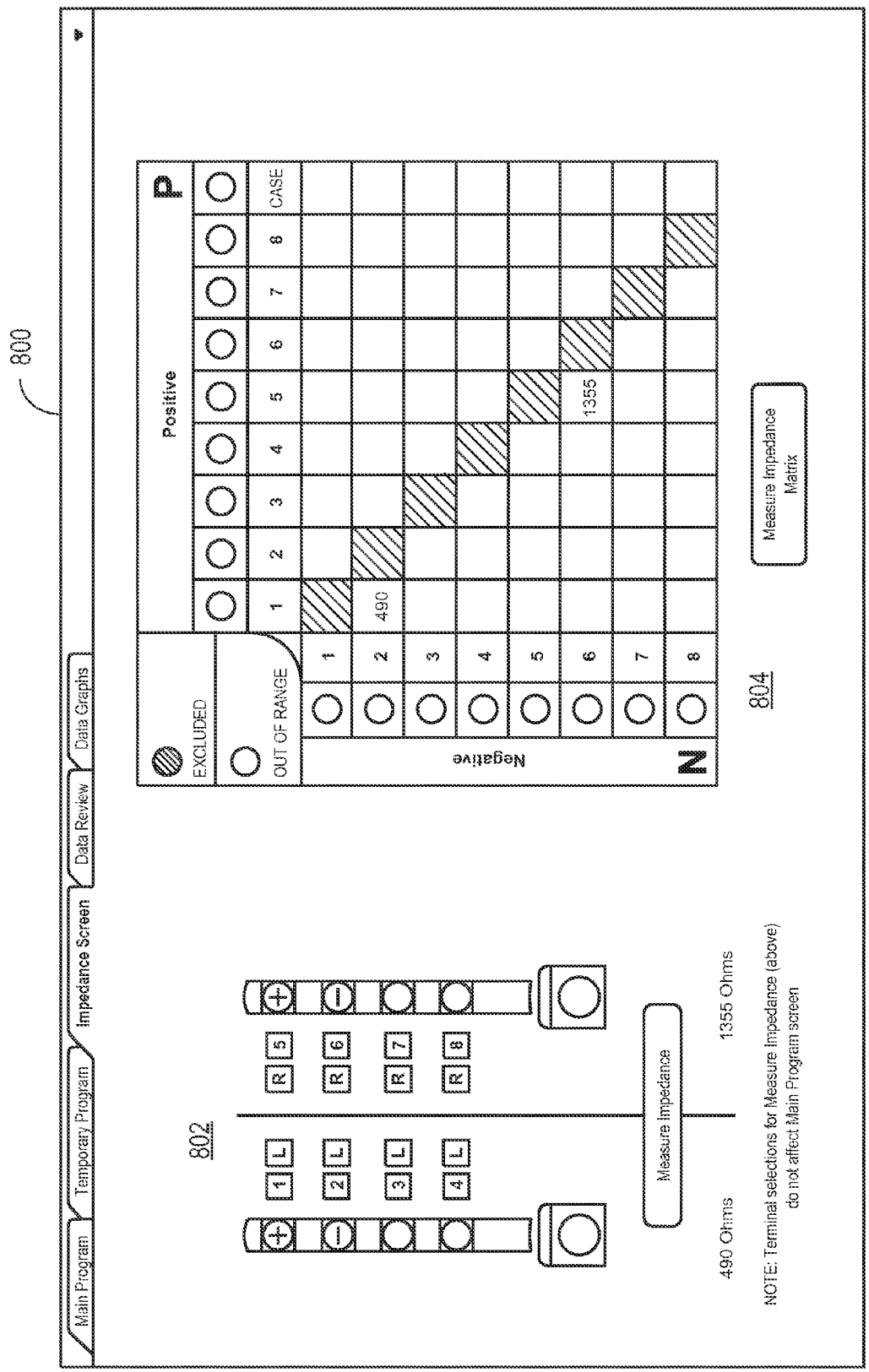
FIG. 7 is an exemplary screenshot illustrating various aspects of the graphical user interface of the software-based programming system of the present invention.

Referring now to FIG. 7, an exemplary graphical user interface of software 600 is described for a stimulator system. FIG. 7 shows impedance screen 800 that is displayed to a physician running software-based programming system 600. Impedance screen 800 includes electrode configuration area 802 and impedance matrix area 804.

Electrode configuration area 802 includes right electrode lead impedance display, left electrode lead impedance display, and Impedance area. Right electrode lead impedance display shows an illustration of four electrodes (numbered 5-8) on the right electrode lead implanted within the subject while left electrode lead impedance display shows the four electrodes (numbered 1-4) on the left electrode lead implanted within the subject. A user may select at which electrode(s) to measure impedance using the respective displays and may change the polarity of each electrode between positive and negative. In the illustrated embodiment, when a session begins, negative electrode 6 on the right lead and negative electrode 2 on the left lead transmit energy to target tissue to stimulate the tissue and positive electrodes 5 and 1, respectively, receive the energy after it has passed through the target tissue.

Impedance area permits a user to select the "Measure Impedance" button which causes the programming system, e.g., via the external programmer, to command the pulse generator to run the routine to measure impedances and then transmit the measured impedances back to the programming system, e.g., via the external programmer. The measured impedances then are displayed for each electrode. As described above, the displayed impedance may be used to determine whether one or more fixation elements on the electrode lead are deployed.

Impedance matrix area 804 includes an impedance matrix and a "Measure Impedance Matrix" button. When pressed, the "Measure Impedance Matrix" button causes the impedance matrix to be populated with the measured impedances in accordance with selections made at electrode configuration area 802. The impedance matrix is populated with the impedance measured between two select electrodes having opposite polarities during the impedance assessment, e.g., based on electrode activation and polarity selected at left electrode lead impedance display and right electrode lead impedance display. The displayed impedances in the impedance matrix may be used to determine whether one or more fixation elements on the electrode lead are deployed. In addition, the impedance measurements may be time stamped. If an electrode shorts out, the IPG may be configured to exclude the nonfunctioning electrode and the time stamp may be used to determine when the electrode shorted out.

In the illustrated embodiment, impedance between electrode 2 (selected to be negative) and electrode 1 (selected to be positive) on the left lead is measured to be 490 Ohms and impedance between electrode 6 (selected to be negative) and electrode 5 (selected to be positive) on the right electrode lead is measured to be 1355 Ohms. Thus, when the Measure Impedance Matrix button is pressed, the software causes 490 to be populated at the intersection of 2 negative and 1 positive and 1355 to be populated at the intersection of 6 negative and 5 positive in the impedance matrix. The impedance matrix also may display when an electrode is excluded or out of range.

As will be readily understood by one of ordinary skill in the art, a user may enter data into the graphical user interface using suitable mechanisms known in the art, such as, entering numbers, letters, and/or symbols via a keyboard or touch screen, mouse, touchpad, selection from a drop-down menu, voice commands, or the like.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for restoring muscle function to the lumbar spine, the system comprising:
   first and second electrodes configured to be implanted in or adjacent to tissue associated with control of the lumbar spine;
   a lead having the first and second electrodes disposed thereon;
   a fixation element coupled to the lead and disposed in proximity to the first electrode, the fixation element configured to transition from a delivery state, wherein the fixation element is positioned adjacent to the first electrode, to a deployed state, wherein the fixation element is spaced apart from the first electrode and is positioned to anchor the lead to an anchor site;
   a pulse generator coupled to the first and second electrodes via the lead, the pulse generator configured to cause the first or second electrode to emit energy such that the second or first electrode, respectively, receives a portion of the emitted energy, the pulse generator further configured to transmit a signal indicative of an impedance measurement based on the energy emitted and the portion of the energy received; and
   software stored on a non-transient computer readable media configured to run on an external computer operatively coupled to the pulse generator, the software configured to cause the external computer to display the impedance measurement and to indicate whether the fixation element is in the delivery state or the deployed state based on the impedance measurement.

2. The system of claim 1, further comprising a second fixation element coupled to the lead distal to the fixation element, wherein the fixation element is angled distally relative to the lead and the second fixation element is angled proximally relative to the lead, and wherein the fixation element and the second fixation element are configured to sandwich the anchor site therebetween.

3. The system of claim 1, further comprising an external programmer coupled to the external computer, the external programmer configured to receive the signal indicative of the impedance measurement from the pulse generator and to transmit the signal to the external computer.

4. The system of claim 3, wherein the external programmer is configured to transfer programming data to the pulse generator.

5. The system of claim 4, wherein the software is configured to permit selection, adjustment, and display of the programming data.

6. The system of claim 4, wherein the programming data comprises at least one of: pulse amplitude, pulse width, stimulation rate, stimulation frequency, ramp timing, cycle timing, session timing, or electrode configuration.

7. The system of claim 4, further comprising a handheld activator configured to transfer a stimulation command to the pulse generator, wherein the stimulation command directs at least one of the first or second electrodes to stimulate the tissue in accordance with the programming data.

8. The system of claim 1, wherein the software is further configured to cause the external computer to display a second impedance measurement based on a second signal.

9. The system of claim 1, wherein the software is configured to determine whether the fixation element is in the delivery state or the deployed state.

10. The system of claim 1, wherein the impedance measurement is indicative of the fixation element being in the delivery state in a range and the impedance measurement is indicative of the fixation element being in the deployed state in a different range.

11. The system of claim 10, wherein the range is between 1501-3500 ohms, 1200-2500 ohms, 1000-2000 ohms, or 750-1750 ohms and the different range is between 500-1500 ohms, 500-1200 ohms, 500-1000 ohms, or 500-750 ohms.

12. A method of verifying deployment of a fixation element in a system for restoring muscle function to the lumbar spine, the method comprising:
   implanting a lead such that an electrode disposed on the lead is positioned in or adjacent to tissue associated with control of the lumbar spine, the lead coupled to a fixation element disposed in proximity to the electrode, the fixation element configured to transition from a delivery state, wherein the fixation element is positioned adjacent to the electrode, to a deployed state, wherein the fixation element is spaced apart from the electrode and is positioned to anchor the lead to an anchor site;
   causing the electrode to stimulate tissue using a pulse generator;
   transmitting a signal indicative of an impedance measurement to an external display;
   displaying the impedance measurement on the external display; and
   determining whether the fixation element is in the delivery state or the deployed state based on the displayed impedance measurement.

13. The method of claim 12, wherein the signal is transmitted from the pulse generator to an external programmer coupled to an external computer having the external display.

14. The method of claim 12, further comprising adjusting the lead if the fixation element is determined to be in the delivery state.